United States Patent [19]

Prusiner et al.

[11] Patent Number: 5,565,186
[45] Date of Patent: Oct. 15, 1996

[54] METHOD OF DETECTING PRIONS IN A SAMPLE AND TRANSGENIC ANIMAL USED FOR SAME

[75] Inventors: Stanley B. Prusiner; Michael R. Scott; Glenn Telling, all of San Francisco, Calif.

[73] Assignee: The Regents of the University of California, Alameda, Calif.

[21] Appl. No.: 242,188

[22] Filed: May 13, 1994

[51] Int. Cl.$^6$ .......................... C12N 15/09; C07H 21/04; A61K 49/00; G01N 33/00
[52] U.S. Cl. .................. 424/9.2; 424/9.1; 435/5; 435/29; 435/69.1; 435/69.7; 435/71.1; 435/172.3; 435/240.21; 435/320.1; 536/23.1; 536/23.4; 536/23.5; 536/23.72; 800/2; 800/DIG. 1
[58] Field of Search ................. 424/9.1, 9.2; 435/172.3, 435/69.1, 5.29, 69.7, 71.1, 240.21, 320.1; 536/23.1, 23.4, 23.5, 24.1, 23.72; 800/2, DIG. 1; 935/6, 42, 53, 55, 70

[56] References Cited

U.S. PATENT DOCUMENTS 5,237,056  8/1993  Fischbach ........................... 536/23.5

FOREIGN PATENT DOCUMENTS

WO93/10227  5/1993  WIPO.

OTHER PUBLICATIONS

Kretzschmar et al., "Molecular Cloning of a Human prion Protein cDNA", *DNA* (1986) 5:315–324.
Scott et al., "Propagation of Prions with Artificial Properties in Transgenic Mice Expressing Chimeric PrP Genes," *Cell* (1993) 73:979–988.
Prusiner et al., "Transgenic Studies Implicate Interactions between Homologous PrP Isoforms in Scrapie Prion Replication," *Cell* (1990) 63:673–686.
Prusiner, "Molecular Biology of Prion Diseases," *Science* (1991) 252:1515–1522.
Bueler et al., "Normal development and behaviour of mice lacking the neuronal cell–surface PrP protein," *Nature* (1992) 356:577–582.
Prusiner et al., "Ablation of the prion protein (PrP) gene in mice prevents scrapie and facilitates production of anti–PrP antibodies," *Proc. Natl. Acad. Sci. USA* (1993) 90:10608–10612.
Prusiner et al., "Prion Diseases and Neurodegeneration," *Ann. Rev. Neurosci.* (1994) 17:311–339.
Westaway et al., "Degeneration of Skeletal Muscle, Peripheral Nerves, and the Central Nervous System in Transgenic Mice Overexpressing Wild–Type Prion Proteins," *Cell* (1994) 76:117–129.
Bolton et al., "Identification of a Protein That Purifies with the Scrapie Prion," *Science* (1982) 218:1309–11.
Prusiner et al, "Further Purification and Characterization of Scrapie Prions," *Biochemistry* (1982) 21:6942–50.
McKinley et al., "A Protease–Resistant Protein Is a Structural Component of the Scrapie Prion," *Cell* (1983) 35:57–62.
Basler et al., "Scrapie and Cellular PrP Isoforms Are Encoded by the Same Chromosomal Gene," *Cell* (1986) 46:417–28.

(List continued on next page.)

*Primary Examiner*—Brian R. Stanton
*Attorney, Agent, or Firm*—Karl Bozicevic; Fish & Richardson P.C.

[57] ABSTRACT

Prions are protein based infectious material that cause of variety of diseases such as Scrapie, bovine spongiform encephalopathy (also known as "Mad Cow" disease), Creutzfeldt Jakob Disease, Kuru, and fatal familial insomnia. The invention is directed to artificial prion genes that are made up of elements of the prion genes of a host and test species. When these artificial prion genes are inserted into a transgenic mouse, the resultant mouse becomes susceptible to infection with prions that infect the test species but do not normally infect mice. The transgenic animals are useful for testing for the presence of prions in a sample.

22 Claims, 4 Drawing Sheets

OTHER PUBLICATIONS

Gajdusek, D.C., "Unconventional Viruses and the Origin and Disappearance of Kuru," *Science* (1977) 197:943–960.

Medori et al., "Fatal Familial Insomnia, a Prion Disease with a Mutation at Codon 178 of the Prion Protein Gene," *N. Engl. J. Med.* (1992) 326:444–449.

Hsaio et al., "Inherited Human Prion Diseases," *Neurology* (1990) 40:1820–1827.

Goldfarb et al., "Fatal Familial Insomnia and Familial Creutzfeldt–Jakob Disease: Disease Phenotype Determined by a DNA Polymorphism," *Science* (1992) 258:806–808.

Locht et al., "Molecular Cloning and Complete Sequence of Prion Protein cDNA from Mouse Brain Infected with the Scrapie Agent," *Proc. Natl. Acad. Sci. USA* (1986) 83:6372–6376.

Patel, "France Reels at Latest Medical Scandal," *New Scientist*, Jul. 31, 1993, p. 4.

Koch et al., "Creutzfeldt–Jakob Disease in a Young Adult with Idiopathic Hypopituitarism," *N. Engl. J. Med.* (1985) 313:731–733.

Buchanan et al., "Mortality, Neoplasia, and Creutzfeldt–Jakob Disease in Patients Treated with Human Pituitary Growth Hormone in the United Kingdom," *BMJ* (1991) 302:824–828.

Lasmezas et al., "Recombinant Human Growth Hormone and Insulin–Like Growth Factor I Induce PRP Gene Expression In PC12 Cells," *Biochem. Biophys. Res. Commun.* (1993) 196:1163–1169.

Gibbs, Jr. et al., "Creutzfeldt–Jakob Disease Infectivity of Growth Hormone Derived from Human Pituitary Glands," *N. Engl. J. Med.* (1993) 328:358–359.

Healy et al., "Creutzfeldt–Jakob Disease After Pituitary Gonadotrophins: The Prion is the Problem," *BMJ* (1993) 307:517–518.

Cochius et al., "Creutzfeldt–Jakob Disease in a Recipient of Human Pituitary–Derived Gonadotrophin," *Aust. N.Z. J. Med.* (1990) 20:592–593.

Cochius et al., "Creutzfeldt–Jakob Disease in a Recipient of Human Pituitary–Derived Gonadotrophin: A Second Case," *J. Neurol. Neurosurg. Psychiatry* (1992) 55:1094–1095.

Nisbet et al., "Creutzfeldt–Jakob Disease in a Second Patient Who Received a Cadaveric Dura Mater Graft," *J. Am. Med. Assoc.* (1989) 261:1118.

Thadani et al., "Creutzfeldt–Jakob Disease Probably Acquired from a Cadaveric Dura Mater Graft," *J. Neurosurg.* (1988) 69:766–769.

Willison et al., "Creutzfeldtz–Jakob Disease Following Cadaveric Dura Mater Graft," *J. Neurosurg. Psychiatric* (1991) 54:940.

Patel, "Placenta Donors to be Screened for Brain Disease", *New Scientist*, Nov. 20, 1993, p. 10.

Gabriel et al., "Molecular Cloning of a Candidate Chicken Prion Protein," *Proc. Natl. Acad. Sci. USA* (1992) 89:9097–9101.

Manuelidis et al., "Interspecies Transmission of Creutzfeldt–Jakob Disease to Syrian Hamsters with Reference to Clinical Syndromes and Strains of Agent," *Proc. Natl. Acad. Sci. USA* (1978) 75:3432–3436.

Manuelidis et al., "Serial Propagation of Creutzfeldt–Jakob Disease in Guinea Pigs," *Proc. Natl. Acad. Sci. USA* (1976) 73:223–227.

Tateishi et al., "Transmission of Chronic Spongiform Encephalopathy with Kuru Plaques from Humans to Small Rodents," *Ann. Neurol.* (1979) 5:581–584.

Collinge et al., "Genetic Predisposition to Iatrogenic Creutzfeldt–Jakob Disease," *Lancet* (1991) 337:1441–1442.

Bueler et al., "Mice Devoid of PrP are Resistant to Scrapie," *Cell* (1993) 73:1339–1347.

Goldmann et al., "Two Alleles of a Neural Protein Gene Linked to Scrapie in Sheep," *Proc. Natl. Acad. Sci. USA* (1990) 87:2476–2480.

Goldmann et al., "Different Forms of the Bovine PrP Gene Have Five or Six Copies of a Short, G–C–Rich Element within the Protein–Coding Exon," *J. Gen. Virol.* (1991) 72:201–204.

Harris et al., "A Prion–like Protein from Chicken Brain Copurifies with an Acetylcholine Receptor–Inducing Activity," *Proc. Natl. Acad. Sci. USA* (1991) 88:7664–7668.

Kretzschmar et al., "Molecular Cloning of a Mink Prion Protein Gene," *J. Gen. Virol.* (1992) 73:2757–2761.

Westaway et al., "Homozygosity for Prion Protein Alleles Encoding Glutamine–171 Renders Sheep Susceptible to Natural Scrapie," *Genes Dev.* (1994) 8:959–969.

Raeber et al., "Attempts to Convert the Cellular Prion Protein into the Scrapie Isoform in Cell–Free Systems," *J. Virol.* (1992) 66:6155–6163.

Stahl et al., "Glycosylinositol Phospholipid Anchors of the Scrapie and Cellular Prion Proteins Contain Sialic Acid," *Biochemistry* (1992) 31:5043–5053.

Hecker et al., "Replication of Distinct Scarpie Prion Isolates is Region Specific in Brains of Transgenic Mice and Hamsters," *Genes Dev.* (1992) 6:1213–1228.

Carlson et al., "Linkage of Protein and Scrapie Incubation Time Genes," *Cell* (1986) 46:503–511.

Hsaio et al., "Linkage of a Prion Protein Missense Variant to Gerstmann–Straussler Syndrome," *Nature* (1989) 338:342–345.

Hsaio et al., "A Prion Protein Variant in a Family with the Telencephalic Form of Gerstmann–Straussler–Scheinker Syndrome," *Neurology* (1991) 41:681–684.

Taraboulos et al., "Regional Mapping of Prion Proteins in Brain," *Proc. Natl. Acad. Sci. USA* (1992) 89:7620–7624.

Brown et al., "'Friendly Fire' in Medicine: Hormones, Homografts, and Cruetzfeldt–Jakob Disease," *Lancet* (1992) 340:24–27.

Kretzschmar, et al., "Molecular Cloning of a Human Prion Protein cDNA," *DNA* (1986) 5:315–324.

Scott et al. 1989. Cell. 59:847–857.

Telling et al. 1994. Proc. Natl. Acad. SCi. USA 91:9936–9940.

Telling et al. 1995. Cell 83:79–90.

| | | | | | | | | | | | | | | | | |
|---|---|---|---|---|---|---|---|---|---|---|---|---|---|---|---|---|
| Mo | Met | Ala | Asn | Leu | Gly | Tyr | Trp | Leu | Leu | Ala | Leu | Phe | Val | Thr | Met | Trp | 16 |
| Hu | | | | | | Cys | | Met | | Val | | | | Ala | Thr | | |

| | | | | | | | | | | | | | | | | |
|---|---|---|---|---|---|---|---|---|---|---|---|---|---|---|---|---|
| Mo | Thr | Asp | Val | Gly | Leu | Cys | Lys | Lys | Arg | Pro | Lys | Pro | Gly | Gly | Trp | Asn | 32 |
| Hu | Ser | | Leu | | | | | | | | | | | | | | |

| | | | | | | | | | | | | | | | | |
|---|---|---|---|---|---|---|---|---|---|---|---|---|---|---|---|---|
| Mo | Thr | Gly | Gly | Ser | Arg | Tyr | Pro | Gly | Gln | Gly | Ser | Pro | Gly | Gly | Asn | Arg | 48 |
| Hu | | | | | | | | | | | | | | | | | |

| | | | | | | | | | | | | | | | | |
|---|---|---|---|---|---|---|---|---|---|---|---|---|---|---|---|---|
| Mo | Tyr | Pro | Pro | Gln | Gly | Gly | --- | Thr | Trp | Gly | Gln | Pro | His | Gly | Gly | Gly | 63 |
| Hu | | | | | | | Gly | Gly | | | | | | | | | |

| | | | | | | | | | | | | | | | | |
|---|---|---|---|---|---|---|---|---|---|---|---|---|---|---|---|---|
| Mo | Trp | Gly | Gln | Pro | His | Gly | Gly | Ser | Trp | Gly | Gln | Pro | His | Gly | Gly | Ser | 79 |
| Hu | | | | | | | | Gly | | | | | | | | Gly | |

| | | | | | | | | | | | | | | | | |
|---|---|---|---|---|---|---|---|---|---|---|---|---|---|---|---|---|
| Mo | Trp | Gly | Gln | Pro | His | Gly | Gly | Gly | Trp | Gly | Gln | Gly | Gly | Gly | Thr | His | 95 |
| Hu | | | | | | | | | | | | | | | | | |

| | | | | | | | | | | | | | | | | |
|---|---|---|---|---|---|---|---|---|---|---|---|---|---|---|---|---|
| Mo | Asn | Gln | Trp | Asn | Lys | Pro | Ser | Lys | Pro | Lys | Thr | Asn | Leu | Lys | His | Val | 111 |
| Hu | Ser | | | | | | | | | | | | Met | | Met | | |

| | | | | | | | | | | | | | | | | |
|---|---|---|---|---|---|---|---|---|---|---|---|---|---|---|---|---|
| Mo | Ala | Gly | Ala | Ala | Ala | Ala | Gly | Ala | Val | Val | Gly | Gly | Leu | Gly | Gly | Tyr | 127 |
| Hu | | | | | | | | | | | | | | | | | |

| | | | | | | | | | | | | | | | | |
|---|---|---|---|---|---|---|---|---|---|---|---|---|---|---|---|---|
| Mo | Met | Leu | Gly | Ser | Ala | Met | Ser | Arg | Pro | Met | Ile | His | Phe | Gly | Asn | Asp | 143 |
| Hu | | | | | | | | | | Ile | | | | | | Ser | |

| | | | | | | | | | | | | | | | | |
|---|---|---|---|---|---|---|---|---|---|---|---|---|---|---|---|---|
| Mo | Trp | Glu | Asp | Arg | Tyr | Tyr | Arg | Glu | Asn | Met | Tyr | Arg | Tyr | Pro | Asn | Gln | 159 |
| Hu | Tyr | | | | | | | | | | | His | | | | | |

| | | | | | | | | | | | | | | | | |
|---|---|---|---|---|---|---|---|---|---|---|---|---|---|---|---|---|
| Mo | Val | Tyr | Tyr | Arg | Pro | Val | Asp | Gln | Tyr | Ser | Asn | Gln | Asn | Asn | Phe | Val | 175 |
| Hu | | | | | | | Met | | Glu | | | | | | | | |

| | | | | | | | | | | | | | | | | |
|---|---|---|---|---|---|---|---|---|---|---|---|---|---|---|---|---|
| Mo | His | Asp | Cys | Val | Asn | Ile | Thr | Ile | Lys | Gln | His | Thr | Val | Thr | Thr | Thr | 191 |
| Hu | | | | | | | | | | | | | | | | | |

| | | | | | | | | | | | | | | | | |
|---|---|---|---|---|---|---|---|---|---|---|---|---|---|---|---|---|
| Mo | Thr | Lys | Gly | Glu | Asn | Phe | Thr | Glu | Thr | Asp | Val | Lys | Met | Met | Glu | Arg | 207 |
| Hu | | | | | | | | | | | | | | | | | |

| | | | | | | | | | | | | | | | | |
|---|---|---|---|---|---|---|---|---|---|---|---|---|---|---|---|---|
| Mo | Val | Val | Glu | Gln | Met | Cys | Val | Thr | Gln | Tyr | Gln | Lys | Glu | Ser | Gln | Ala | 223 |
| Hu | | | | | | | Ile | | | | | | Glu | Arg | | | |

| | | | | | | | | | | | | | | | | |
|---|---|---|---|---|---|---|---|---|---|---|---|---|---|---|---|---|
| Mo | Tyr | Tyr | Asp | Gly | Arg | Arg | Ser | Ser | Ser | Thr | Val | Leu | Phe | Ser | Ser | Pro | 239 |
| Hu | | | Gln | --- | --- | | Gly | | | Met | | | | | | | |

| | | | | | | | | | | | | | | |
|---|---|---|---|---|---|---|---|---|---|---|---|---|---|---|
| Mo | Pro | Val | Ile | Leu | Leu | Ile | Ser | Phe | Leu | Ile | Phe | Leu | Ile | Val | Gly | 254 |
| Hu | | | | | | | | | | | | | | | | |

Figure 3: Predicted amino acid sequence of mouse PrP and the amino acid differences between mouse and human PrP.

```
Mo  Met Ala Asn Leu --- --- Gly Tyr Trp Leu Leu Ala Leu Phe Val Thr  14
Bo      Val Lys Ser His Ile     Ser     Ile     Val             Ala

Mo  Met Trp Thr Asp Val Gly Leu Cys Lys Lys Arg Pro Lys Pro Gly Gly  30
Bo          Ser

Mo  --- Trp Asn Thr Gly Gly Ser Arg Tyr Pro Gly Gln Gly Ser Pro Gly  45
Bo

Mo  Gly Asn Arg Tyr Pro Pro Gln Gly Gly --- Thr Trp Gly Gln Pro His  60
Bo           .                           Gly Gly

Mo  Gly Gly Gly Trp Gly Gln Pro His Gly Gly Ser Trp Gly Gln Pro His  76
Bo                                              Gly

Mo  Gly Gly Ser Trp Gly Gln Pro His Gly Gly Gly Trp Gly Gln --- ---  90
Bo          Gly                                               Pro His

Mo  --- --- --- --- --- --- Gly Gly Gly Thr His Asn Gln Trp Asn Lys 100
Bo  Gly Gly Gly Gly Trp Gly Gln                 Gly

Mo  Pro Ser Lys Pro Lys Thr Asn Leu Lys His Val Ala Gly Ala Ala Ala 116
Bo                              Met

Mo  Ala Gly Ala Val Val Gly Gly Leu Gly Gly Tyr Met Leu Gly Ser Ala 132
Bo

Mo  Met Ser Arg Pro Met Ile His Phe Gly Asn Asp Trp Glu Asp Arg Tyr 148
Bo                  Leu                  Ser     Tyr

Mo  Tyr Arg Glu Asn Met Tyr Arg Tyr Pro Asn Gln Val Tyr Tyr Arg Pro 164
Bo                      His

Mo  Val Asp Gln Tyr Ser Asn Gln Asn Asn Phe Val His Asp Cys Val Asn 180
Bo

Mo  Ile Thr Ile Lys Gln His Thr Val Thr Thr Thr Lys Gly Glu Asn 200
Bo          Val     Glu

Mo  Phe Thr Glu Thr Asp Val Lys Met Met Glu Arg Val Val Glu Gln Met 212
Bo                          Ile

Mo  Cys Val Thr Gln Tyr Gln Lys Glu Ser Gln Ala Tyr Tyr Asp Gly Arg 228
Bo                                                          Gln ---

Mo  Arg Ser Ser Ser Thr Val Leu Phe Ser Ser Pro Pro Val Ile Leu Leu 244
Bo  --- Gly Ala         Val Ile

Mo  Ile Ser Phe Leu Ile Phe Leu Ile Val Gly                         254
Bo
```

Figure 4: Predicted amino acid sequence of mouse PrP and the amino acid differences between mouse and bovine PrP

| | | | | | | | | | | | | | | | |
|---|---|---|---|---|---|---|---|---|---|---|---|---|---|---|---|
| Mo | Met | Ala | Asn | Leu | --- | --- | Gly | Tyr | Trp | Leu | Leu | Ala | Leu | Phe | Val | Thr | 14 |
| Sh | | Val | Lys | Ser | His | Ile | | Ser | | Ile | | Val | | | | Ala |

Mo Met Ala Asn Leu --- --- Gly Tyr Trp Leu Leu Ala Leu Phe Val Thr 14
Sh     Val Lys Ser His Ile     Ser     Ile     Val             Ala

Mo Met Trp Thr Asp Val Gly Leu Cys Lys Lys Arg Pro Lys Pro Gly Gly 30
Sh         Ser

Mo --- Trp Asn Thr Gly Gly Ser Arg Tyr Pro Gly Gln Gly Ser Pro Gly 45
Sh

Mo Gly Asn Arg Tyr Pro Pro Gln Gly Gly --- Thr Trp Gly Gln Pro His 60
Sh                                 Gly Gly

Mo Gly Gly Gly Trp Gly Gln Pro His Gly Gly Ser Trp Gly Gln Pro His 76
Sh                                         Gly

Mo Gly Gly Ser Trp Gly Gln Pro His Gly Gly Gly --- Trp Gly Gln Gly 91
Sh                                             Gly

Mo Gly Gly Thr His Asn Gln Trp Asn Lys Pro Ser Lys Pro Lys Thr Asn 107
Sh     Ser --- His Ser

Mo Leu Lys His Val Ala Gly Ala Ala Ala Ala Gly Ala Val Val Gly Gly 123
Sh Met

Mo Leu Gly Gly Tyr Met Leu Gly Ser Ala Met Ser Arg Pro Met Ile His 139
Sh                                                             Leu

Mo Phe Gly Asn Asp Trp Glu Asp Arg Tyr Tyr Arg Glu Asn Met Tyr Arg 155
Sh                     Tyr

Mo Tyr Pro Asn Gln Val Tyr Tyr Arg Pro Val Asp Gln Tyr Ser Asn Gln 171
Sh

Mo Asn Asn Phe Val His Asp Cys Val Asn Ile Thr Ile Lys Gln His Thr 187
Sh                                             Val

Mo Val Thr Thr Thr Thr Lys Gly Glu Asn Phe Thr Glu Thr Asp Val Lys 203
Sh                                                             Ile

Mo Met Met Glu Arg Val Val Glu Gln Met Cys Val Thr Gln Tyr Gln Lys 219
Sh Ile                                 Ile                     Arg

Mo Glu Ser Gln Ala Tyr Tyr Asp Gly Arg Arg Ser Ser Ser Thr Val Leu 235
Sh                         Gln --- ---         Gly Ala     Val Ile

Mo Phe Ser Ser Pro Pro Val Ile Leu Leu Ile Ser Phe Leu Ile Phe Leu 251
Sh

Mo Ile Val Gly                                                      254
Sh

Figure 5: Predicted amino acid sequence of mouse PrP and the amino acid differences between mouse and sheep PrP 5,565,186

METHOD OF DETECTING PRIONS IN A SAMPLE AND TRANSGENIC ANIMAL USED FOR SAME

GOVERNMENT RIGHTS

The United States Government may have certain rights in this application pursuant to Grant Nos. NS14069, AG02132, NS22786, AG08967 and AG10770 awarded by the National Institutes of Health.

FIELD OF THE INVENTION

This invention relates generally to chimeric genes, methods of assaying and to transgenic animals used in such assays. More specifically, this invention relates to artificial and chimeric PrP genes, assaying samples for pathogenic prions, and to transgenic mice containing an artificial or chimeric PrP gene.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, aprion which infects one species of animal (e.g., a human) will not infect another (e.g., a mouse).

A major step in the study of prions and the diseases that they cause was the discovery and purification of a protein designated prion protein ("PrP") [Bolton et al., Science 218:1309–11 (1982); Prusiner et al., Biochemistry 21:6942–50 (1982); McKinley et al., Cell 35:57–62 (1983)]. Complete prion protein-encoding genes have since been cloned, sequenced and expressed in transgenic animals. $PrP^C$ is encoded by a single-copy host gene [Basler et al., Cell 46:417–28 (1986)] and is normally found at the outer surface of neurons. A leading hypothesis is that prion diseases result from conversion of $PrP^C$ into a modified form called $PrP^{Sc}$. However, the actual biological or physiological function of $PrP^C$ is not known.

It appears that the scrapie isoform of the prion protein ($PrP^{Sc}$) is necessary for both the transmission and pathogenesis of the transmissible neurodegenerative diseases of animals and humans. See Prusiner, S.B., "Molecular biology of prion disease," Science 252:1515–1522 (1991). The most common prion diseases of animals are scrapie of sheep and goats and bovine spongiform encephalopathy (BSE) of cattle [Wilesmith, J. and Wells, Microbiol. Immunol. 172:21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D.C., Science 197:943–960 (1977); Medori et al., N. Engl. J. Med. 326:444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., Neurology 40:1820–1827 (1990); Goldfarb et al., Science 258:806–808 (1992); Kitamoto et al., Proc. R. Soc. Lond. (In press) (1994)]. Iatrogenic CJD has been caused by human growth hormone derived from cadaveric pituitaries as well as dura mater grafts [Brown et al., Lancet 340:24–27 (1992)]. Despite numerous attempts to link CJD to an infectious source such as the consumption of scrapie infected sheep meat, none has been identified to date [Harries-Jones et al., J. Neurol. Neurosurg. Psychiatry 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M.P., Slow Transmissible Diseases of the Nervous System, Vol. 1, S.B. Prusiner and W.J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into non-human primates and that the animals be observed for disease that was predicted to occur after a prolonged incubation period [Hadlow, W.J., Lancet 2:289–290 (1959)]. Seven years later, Gajdusek, Gibbs and Alpers demonstrated the transmissibility of kuru to chimpanzees after incubation periods ranging form 18 to 21 months [Gajdusek et al., Nature 209:794–796 (1966)]. The similarity of the neuropathology of kuru with that of CJD [Klatzo et al., Lab Invest. 8:799–847 (1959)] prompted similar experiments with chimpanzees and transmissions of disease were reported in 1968 [Gibbs, Jr. et al., Science 161:388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using non-human primates, some cases of human prion disease have been transmitted to rodents but apparently with less regularity [Gibbs, Jr. et al., Slow Transmissible Diseases of the Nervous System, Vol. 2, S.B. Prusiner and W.J. Hadlow, eds. (New York: Academic Press), pp. 87–110 (1979); Tateishi et al., Prion Diseases of Humans and Animals, Prusiner et al., eds. (London: Ellis Horwood), pp. 129–134 (1992)].

The infrequent transmission of human prion disease to rodents has been cited as an example of the "species barrier" first described by Pattison in his studies of passaging the scrapie agent between sheep and rodents [Pattison, I.H., NINDB Monograph 2, D.C. Gajdusek, C.J. Gibbs Jr. and M.P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott et al., Cell 59:847–857 (1989)]. SHaPrP differs from MoPrP (SEQ ID NO:1) at 16 positions out of 254 amino acid residues [Basler et al., Cell 46:417–428 (1986); Locht et al., Proc. Natl. Acad. Sci. USA 83:6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. The seriousness of the health risk resulting from the lack of such a test is exemplified below.

More than 45 young adults previously treated with HGH derived from human pituitaries have developed CJD [Koch et al., *N. Engl. J. Med.* 313:731–733 (1985); Brown et al., *Lancet* 340:24–27 (1992); Fradkin et al., *JAMA* 265:880–884 (1991); Buchanan et al., *Br. Med. J.* 302:824–828 (1991)]. Fortunately, recombinant HGH is now used, although the seemingly remote possibility has been raised that increased expression of wtPrP$^C$ stimulated by high HGH might induce prion disease [Lasmezas et al., *Biochem. Biophys. Res. Commun.* 196:1163–1169 (1993)]. That the HGH prepared from pituitaries was contaminated with prions is supported by the transmission of prion disease to a monkey 66 months after inoculation with a suspect lot of HGH [Gibbs, Jr. et al., *N. Engl. J. Med.* 328:358–359 (1993)]. The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone [Healy et al., *Br. J. Med.* 307:517–518 (1993); Cochius et al., *Aust. N.Z. J. Med.* 20:592–593 (1990); Cochius et al., *J. Neurol. Neurosurg. Psychiatry* 55:1094–1095 (1992)] as well as at least 11 patients receiving dura mater grafts [Nisbet et al., *J. Am. Med. Assoc.* 261:1118 (1989); Thadani et al., *J. Neurosurg.* 69:766–769 (1988); Willison et al., *J. Neurosurg. Psychiatric* 54:940 (1991); Brown et al., *Lancet* 340:24–27 (1992)]. These cases of iatrogenic CJD underscore the need for screening pharmaceuticals that might possibly be contaminated with prions.

Recently, two doctors in France were charged with involuntary manslaughter of a child who had been treated with growth hormones extracted from corpses. The child developed Creutzfeldt-Jakob Disease. (See New *Scientist*, Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist*, Nov. 20, 1993, page 10.) In view of such, there clearly is a need for a convenient, cost-effective assay for testing sample materials for the presence of prions which cause CJD. The present invention offers such an assay.

SUMMARY OF THE INVENTION

The invention includes an artificial PrP gene, a transgenic animal containing the artificial gene or elevated expression of a PrP gene from a genetically diverse animal, and assay methodology which uses the transgenic animal to detect pathogenic prions in a sample. The artificial gene includes a sequence such that when it is inserted into the genome of an animal (such as a mouse), the animal is rendered susceptible to infection with prions which normally would infect only a specific species of genetically diverse animal (such as a human, cow, sheep, pig, chicken, cat or dog). The artificial PrP gene may be comprised partially or completely of an artificial polynucleotide sequence, i.e. codon sequences not present in any native PrP gene sequence. Alternatively, the artificial gene may be comprised of the codon sequence of a host animal with one or more codon substitutions being made wherein the substitutions are preferably corresponding PrP gene codons from a genetically diverse animal, meaning that PrP gene differs from the PrP gene of the host animal by 20 or more codons. Transgenic animals containing elevated levels of expression of the PrP gene which can be obtained for example, by over expression of the gene with an enhanced promoter and/or with high copy numbers of the natural PrP gene of a genetically diverse animal are also disclosed.

Pathogenic prions in a sample can be detected by injecting the sample to be tested into a transgenic mouse. In one preferred example the mouse genome includes a chimeric PrP gene which gene includes a portion of a gene of the animal (e.g. human) in danger of infection from prions in the sample. For example, Creutzfeldt Jakob Disease (CJD) is a fatal neurodegenerative disease of humans caused by prions. Preferred transgenic (Tg) mice disclosed herein express a chimeric prion protein (PrP) in which a segment of mouse (Mo) PrP was replaced with the corresponding human (Hu) PrP sequence. The chimeric PrP designated MHu2MPrP, differs from MoPrP (SEQ ID NO:1) by 9 codons between codons 96 and 167. All of the Tg(MHu2MPrP) mice injected with human prions developed neurologic disease. More specifically, the transgenic mice of the invention developed the disease ~200 days after inoculation with brain homogenates from three CJD patients. When inoculated with CJD prions, MHu2MPrP$^{Sc}$ was formed; in contrast MoPrP$^{Sc}$ was produced if Mo prions were inoculated. Tg(MHu2MPrP) mice disclosed herein are useful in the diagnosis, prevention and treatment of human prion diseases. Transgenic mice containing the artificial PrP gene or elevated levels of expression of a native PrP gene from a genetically diverse animal can be used to test samples for prions which might infect such animals. The transgenic mice disclosed herein consistently develop the adverse effects of such prions in a relatively short time and are substantially cheaper and easier to maintain than are currently used primate models.

An object of the invention is to provide a gene which may be artificial or chimeric which gene when inserted into the genome of one animal (e.g., a mouse) will render the mammal susceptible to infections from prions which naturally only infect a genetically diverse mammal, e.g., human, bovine or ovine.

Another object of the invention is to provide an assay for the detection of prions in a sample.

Another object of the invention is to provide a transgenic animal wherein a host animal includes a genome which has been genetically and artificially transformed to include either the artificial PrP gene of the present invention or elevated levels of expression of a native PrP gene obtained by an enhanced promoter or a high copy number of a native PrP gene of a genetically diverse test animal, such as a human, cow, sheep, pig, dog, cat or chicken.

A feature of the invention is that the PrP gene of the host animal can be altered by replacing codons with codons of a test animal at the same relative position which differ from the codons of the host animal, up to and including replacing all the differing codons.

Another object is to provide an artificial PrP gene wherein one or more codons (preferably 1–39 codons) of the PrP gene of a host animal (e.g. a mouse) is replaced with codons of the PrP gene of a genetically diverse test animal (e.g. a human, cow or sheep) in a manner so as to render the host animal susceptible to infection with prions which normally infect only the genetically diverse test animal.

Another object is to provide a chimeric gene comprised of codons encoding the C- and N- terminus of one species of mammal and middle codons of another species of mammal.

Another object of the invention is to provide a transgenic host mammal such as a mouse, rat or hamster which includes a chimeric PrP gene which gene includes a portion of the PrP gene from another animal, such as a human, cow, sheep, cat or dog.

Another object of the invention is to provide a transgenic host animal which includes elevated levels of expression of a native PrP gene of a genetically diverse animal wherein the elevated levels of expression are obtained by the inclusion of a high copy number of the PrP gene of the genetically diverse mammal and/or fusing an enhanced promoter to the PrP gene of the genetically diverse animal.

An advantage of the present invention is that the transgenic mouse can be used to assay for the presence of prions in a sample in a manner which is substantially faster, more efficient and cheaper than presently available assay methods.

Another advantage is that transgenic mice inoculated with prions of humans can be used as test animals for testing drugs for efficacy in the treatment of humans suffering from diseases resulting from infection with prions.

Another advantage is that the transgenic mice can detect prions in a sample at very low levels, e.g., 1 part per million, and even as low as 1 part per billion.

Still another advantage is that the mice provide an assay which is highly accurate, i.e., does not provide false positives and consistently determines the presence of prions.

Yet another advantage is that by increasing the copy number of the gene of the invention in a transgenic mammal, the incubation time for prion caused disease is decreased.

A feature of the present invention is that the transgenic mice injected with a sample containing pathogenic prions will consistently develop the disease effects of the prions within a relatively short time, e.g. about 200 days ±50 days after injection or less.

Another feature is that an artificial gene of the invention preferably contains codons of the PrP gene of a host animal (such as a mouse) with some (but not all) of the codons which differ from the mouse and a second genetically diverse test mammal (such as a human) replacing codons of the first mammal at the same relative positions.

These and other objects, advantages, and features of the invention will become apparent to those persons skilled in the art upon reading the details of the chimeric gene, assay method, and transgenic mouse as more fully described below.

BRIEF DESCRIPTION OF THE DRAWINGS

FIG. 3 shows the amino acid sequence of mouse PrP (SEQ ID NO:1) along with specific differences between mouse PrP (SSEQ ID NO:1) and human PrP (SEQ ID NO:2);

FIG. 4 shows the amino acid sequence of mouse PrP (SEQ ID NO:1)and specifically shows differences between mouse PrP (SEQ ID NO:1) and bovine PrP (SEQ ID NO:3); and FIG. 5 shows the amino acid sequence of mouse PrP (SEQ ID NO:1)and specifically shows differences between mouse PrP (SEQ ID NO:1) and ovine PrP (SEQ ID NO:4).

DETAILED DESCRIPTION OF PREFERRED EMBODIMENTS

Figure 1:
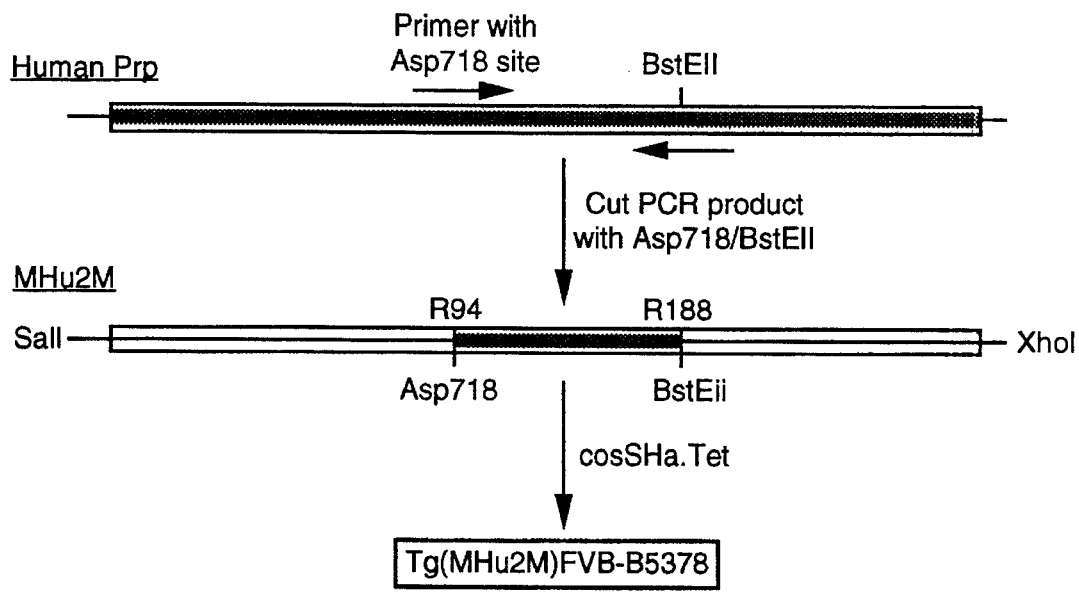
FIG. 1 is a schematic drawing showing the construction of a chimeric MHu2M gene and a transgenic mouse containing same.

Before the present artificial gene, assay methodology and transgenic animal used in the assay are described, it is to be understood that this invention is not limited to particular assay methods, chimeric and artificial genes or transgenic mice described, as such methods, genes and mice may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The term "prion" shall mean an infectious particle known to cause diseases (spongiform encephalopathies) in humans and animals. The term "prion" is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The term "PrP gene" refers generally to any gene of any species which encodes any form of a prion protein. Some commonly known PrP sequences are described in Gabriel et al., *Proc. Natl, Acad. Sci. USA* 89:9097–9101 (1992) which is incorporated herein by reference to disclose and describe such sequences.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 3, 4 and 5 with one or more different replacement codons selected from the codons shown in these Figures for humans, cows and sheep replacing mouse codons at the same position, with the proviso that not all the mouse codons are replaced with differing human, cow or sheep codons. Artificial PrP genes of the invention can include not only codons of genetically diverse animals but may include codons and codon sequences not associated with any native PrP gene but which, when inserted into an animal render the animal susceptible to infection with prions which would normally only infect a genetically diverse animal.

The terms "chimeric gene," "chimeric PrP gene" and the like are used interchangeably herein to mean an artificially constructed gene containing the codons of a host animal such as a mouse with one or more of the codons being replaced with corresponding codons from a genetically diverse test animal such as a human, cow or sheep. In one specific example the chimeric gene is comprised of the starting and terminating sequence (i.e., N- and C- terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues.

The terms "host animal" and "host mammal" are used to describe animals which will have their genome genetically and artificially manipulated so as to include genetic material which is not naturally present within the animal. For example, host animals include mice, hamsters and rats which have their PrP gene altered by the insertion of an artificial gene of the present invention or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal. This is done by including PrP gene sequences of the test animal into the host animal and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "susceptible to infection" and "susceptible to infection by prions" and the like are used interchangeably herein to describe a transgenic test animal of the invention which has an 80% or greater, preferably 98% or greater, and most preferably a 100% chance of developing a disease if inoculated with prions which would normally only infect a genetically diverse test animal. The terms are used to describe a transgenic animal of the invention such as a transgenic mouse Tg(MHu2M) which, without the chimeric PrP gene, would not be susceptible to infection with a human prion (less than 20% chance of infection) but with the chimeric gene is susceptible to infection with human prions (80% to 100% chance of infection).

The term "incubation time" shall mean the time from inoculation of an animal with a prion until the time when the animal first develops detectable symptoms of disease resulting from the infection. A reduced incubation time is one year or less, preferable about 200 days ±50 days or less, more preferably about 50 days ±20 days or less.

Abbreviations used herein include:

CNS for central nervous system;

BSE for bovine spongiform encephalopathy;

CJD for Creutzfeldt-Jakob Disease;

FFI for fatal familial insomnia;

GSS for Gerstmann-Strassler-Scheinker Disease;

Hu for human;

HuPrP for a human prion protein;

Mo for mouse;

MoPrP for a mouse prion protein;

SHa for a Syrian hamster;

SHaPrP for a Syrian hamster prion protein;

Tg for transgenic;

Tg(SHaPrP) for a transgenic mouse containing the PrP gene of a Syrian hamster;

Tg(HuPrP) for transgenic mice containing the complete human PrP gene;

Tg(ShePrP) for transgenic mice containing the complete sheep PrP gene;

Tg(BovPrP) for transgenic mice containing the complete cow PrP gene;

$PrP^{Sc}$ for the scrapie isoform of the prion protein;

$MoPrP^{Sc}$ for the scrapie isoform of the mouse prion protein;

MHu2M for a chimeric mouse/human PrP gene wherein a region of the mouse PrP gene is replaced by a corresponding human sequence which differs from mouse PrP at 9 codons;

Tg(MHu2M) mice are transgenic mice of the invention which include the MHu 2M gene;

$MHu2MPrP^{Sc}$ for the scrapie isoform of the chimeric human/mouse PrP gene;

$PrP^{CJD}$ for the CJD isoform of a PrP gene;

$Prn-p^{0/0}$ for ablation of both alleles of the MoPrP gene;

$Tg(SHaPrP^{+/0})81/Prn-p^{0/0}$ for a particular line (81) of transgenic mice expressing SHaPrP, +/0 indicates heterozygous;

GENERAL ASPECTS OF THE INVENTION

The present invention includes several aspects including: (1) an artificial gene comprised of codon sequences which when inserted into the genome of a host animal (e.g. a mouse or hamster) will render the animal susceptible to infection with prions which normally infect only a genetically diverse test animal (e.g. a human, cow or sheep), thereby including genes wherein one or more codons of a naturally occurring PrP gene of a host animal are replaced with corresponding codons of a genetically diverse test animal; (2) a chimeric gene which gene is comprised of the PrP sequence of a gene of a host mammal of a first species (preferably a mouse or hamster) which gene has been modified to include a corresponding segment of a PrP gene of a test animal, preferably a mammal such as a human, cow or sheep; (3) a transgenic mammal containing an artificial gene of the invention such as a transgenic mouse including a chimeric PrP gene wherein a portion of the mouse gene is replaced with a corresponding portion of a human PrP gene thereby rendering the mouse susceptible to infection with human prions; (4) a transgenic mammal with elevated levels of expression of a PrP gene of a genetically diverse mammal wherein the elevated levels of expression are obtained by incorporating a high copy number (30 or more) of a native PrP gene of a genetically diverse test animal and/or the inclusion of an enhanced promoter operatively fused to the PrP gene of a genetically diverse animal; (5) a method of determining whether a sample is infected with prions which method involves inoculating a transgenic mammal of the invention with a sample to be tested and observing the mammal for a period of time sufficient to determine if the mammal develops symptoms of a disease normally associated with prions; (6) a method of testing the efficacy of a drug in the treatment of disease developed as a result of infection with prions comprising administering a drug to be tested to a transgenic animal infected with prions and observing and/or testing the mammal to determine if the drug aids in treating or slowing the progress of the disease or its symptoms; and (7) a method for determining the cause of death of an animal comprising inoculating a transgenic mammal of the invention with body fluid or tissue such as extracted brain tissue from the animal which has died and observing the transgenic animal in order to determine if the transgenic animal develops symptoms of prion infections.

Preferred host animals are mice and hamsters, with mice being most preferred in that there exists considerable knowledge on the production of transgenic animals. Other possible host animals include those belonging to a genus selected from Mus (e.g. mice), Rattus (e.g. rats), Oryctolagus (e.g. rabbits), and Mesocricetus (e.g. hamsters). The host PrP gene can be changed to include codons from genetically diverse PrP genes from test animals belonging to a genus selected from Bos, Ovis, Sus and Homo. Preferably, a mouse host PrP gene is changed to include codons from a human, cow or sheep PrP gene, with human being most preferred.

The genetic material which makes up the PrP gene is known for a number of different species of animals (see Gabriel et al., *Proc. Natl. Acad. Sci, USA* 89:9097–9101 (1992)). Further, there is considerable homology between the PrP genes in different mammals. For example, see the amino acid sequence of mouse PrP (SEQ ID NO:1) compared to human (SEQ ID NO:2), cow (SEQ ID NO:3)and sheep (SEQ ID NO:4) PrP in FIGS. 3, 4 and 5 wherein only the differences are shown. Further, note that the segment of a PrP gene used to create the MHu2M gene of the present invention will result in encoding of protein which shows a difference between the human and a mouse protein of only nine residues. Although there is considerable genetic homology with respect to PrP genes, the differences are significant in some instances. More specifically, due to small differences in the protein encoded by the PrP gene of different mammals, a prion which will infect one mammal (e.g. a human) will not normally infect a different mammal (e.g. a mouse). Due to this "species barrier", it is not generally possible to use normal, i.e. non-transgenic animals such as mice to determine whether a particular sample contains prions which would normally infect a different species of animal such as a human. The present invention solves this problem in a surprising manner.

Relationships—PrP genes:copy numbers:genetic diversity

We recognized that commercially useful transgenic animals would, preferably, be small and easy to reproduce; thus, host animals such as mice, hamsters and rats are preferred, with mice being most preferred. We also recognized that, in order for the transgenic animals to be useful, it would be necessary for the animals to be susceptible to infection with prions which normally infect only genetically diverse test animals, and in particular animals of commercial significance for testing, such as humans, cows, sheep, pigs, cats, dogs and chickens, with humans being most preferred. Next, we recognized that, for the transgenic animals to be useful in a practical and commercial sense, it would be necessary for the animals to demonstrate symptoms of the disease within a relatively short period after inoculation, and for a very high percentage of the animals to demonstrate symptoms of the disease after inoculation.

In producing a transgenic animal having the above-described characteristics, we noted a number of relationships of significance. First, when the entire PrP gene of the host animal (such as a mouse) is replaced with the entire PrP gene of a test animal (such as a human), the resulting transgenic animal (with a low copy number of human PrP genes) is not susceptible to infection with human prions. Second, when only some of the codons differing between the host and the test animal are switched, the resulting transgenic animal is susceptible to infection with prions which normally only infect the test animal.

Third, we noticed that, as the copy number of the artificial gene in the transgenic animal is increased, the incubation time decreases. With this knowledge, we deduced that it is possible to produce a transgenic animal wherein all of the PrP gene of the host animal is replaced with the PrP gene of a test animal to obtain a useful transgenic animal which is susceptible to infection with prions which normally only infect the test animal by substantially increasing the copy number of the test animal's PrP gene in the host animal. For example, a transgenic mouse which includes the entire PrP gene of a human in a relatively low copy number (e.g. 1 to 4) is not susceptible to infection with human prions. However, if the transgenic mouse includes a very high copy number of a human gene (e.g. 30–300 copies), the resulting transgenic animal is susceptible to infection with human prions. Further, when a host animal such as a mouse has only a portion of its PrP gene replaced with a corresponding portion of a test animal such as a human, the resulting transgenic animal is highly susceptible to infection with prions which normally infect only the test animal. This is true even if the chimeric gene is present in the transgenic animal in a relatively low copy number (e.g. 1 to 4 copies) resulting in low expression of MHu2M $PrP^C$.

Based on the above, it can be understood that the preferred transgenic animals of the invention are animals such as mice which include only a portion, but not all, of their PrP gene replaced with a corresponding portion of the PrP gene of a test animal. Further, it is preferable to include such chimeric genes within the transgenic animal in a relatively high copy number, in that increasing the copy number tends to decrease the incubation time for the disease once the animal is inoculated with material containing prions. Notwithstanding such, we now understand that, when the copy number is increased to very high numbers (e.g. 100 copies and above), the transgenic animals may spontaneously demonstrate symptoms of prion disease. Thus, a most preferred transgenic animal of the invention will include a chimeric PrP gene in a sufficiently high copy number so as to shorten the incubation time (e.g. 50 copies ±25) but in a sufficiently low number so as to not initiate spontaneous symptoms characteristic of prion diseases (e.g., not more than 100 copies). It will be understood by those skilled in the art that the number of copies necessary in order to obtain elevated levels of expression of the PrP gene will vary depending upon the particular gene inserted into the particular host. Adjustments can be made to reduce the copy number if the resulting transgenic animals become spontaneously ill. Alternatively adjustments can be made to increase the copy number if the resulting transgenic animals are not subject to infection with prions which normally infect only a genetically diverse animal. Further, adjustments can be made with respect to the use of specific types of enhanced promoters in order to elevate the levels of expression without increasing copy numbers. Specific types of enhanced promoters are known such as neuronal enolase promoters which would provide enhanced expression to the PrP gene without increased copy numbers. The enhanced promoters may operate constitutively or inducibly.

Next, we noted that the ability to successfully produce a transgenic animal related, in part, to the genetic diversity between the host animal and the test animal as regards their respective PrP genes. For example, the PrP gene of a mouse and a hamster are relatively similar in that they differ only at 16 codons out of a total of 254 codons. When the genetic similarity of the PrP genes are this close, it is possible to include the entire PrP gene sequence of the test animal into the host animal and render the host animal susceptible to prions which normally only infect the test animal. However, such is not the case when the host animal and test animal are genetically diverse, i.e. differ in PrP genes by 20 or more codons. Thus, when a mouse PrP gene is completely replaced with a genetically diverse PrP gene, such as that of a human, the resulting transgenic mouse will not be susceptible to infection with human prions unless the human gene is present in the mouse in a relatively high copy number.

To solve the problem of being able to decrease the copy number such that the animal would not spontaneously become sick, and yet allow the animal to become sick when inoculated with human prions, we created a chimeric gene which includes only a portion of the human PrP gene in the mouse PrP gene. A more specific description of how the species barrier was broken in accordance with the present invention is provided below.

Species Barrier Broken

The transmission of human CJD to apes and monkeys 1.5–3 years after intracerebral inoculation provided considerable interest in the causes of neurodegenerative diseases [Gibbs, Jr. et al., *Science* 161:388–389 (1968)]. Humans are not genetically diverse from apes and monkeys which accounts for the cross-species infectivity, although with a long incubation time. While the high cost of caring for nonhuman primates prevented extensive studies of the human prion diseases, the transmissibility of these diseases stimulated studies of the animal prion analogues in rodents [Manuelidis et al., *Proc. Natl. Acad. Sci. USA* 75:3422–3436 (1978); Manuelidis et al., *Proc. Natl. Acad. Sci. USA* 73:223–227 (1976); Tateishi et al., *Ann, Neurol.* 5:581–584 (1979)].

The present disclosure opens a new frontier in the investigation of the human prion diseases since transmission studies can now be performed relatively rapidly in genetically altered mammals such as Tg(MHu2M) mice that are relatively inexpensive to maintain. For the first time, endpoint titrations of prions in multiple human body tissues and fluids can be performed and standard curves constructed for more economical incubation time assays. The information derived from such studies of human prions will be useful in the management of CJD patients who are thought to pose some risk to relatives, physicians, nurses and clinical laboratory technicians [Berger et al., *Neurology* 43:205–206 (1993); Ridley et al., *Lancet* 341:641–642 (1993)].

In studies of human prion diseases with apes and monkeys, the use of one or two, or rarely three, animals as recipients for a single inoculum has presented a significant problem in evaluating the transmissibility of a particular inoculum from an individual patient. The Tg(MHu2M) mice described here obviate many of the problems created by using nonhuman primates.

These results demonstrate the "universality" of the MHu2M transgene for transmission studies with other types of transgenic animals and other prion inocula. For example, it may be most efficient to use mice expressing MHu2MPrP transgenes coding for either a methionine or valine at codon 129, and by doing so, match the genotype of the Tg mouse (with respect to codon 129) with the genotype of the individual from which the inoculum is derived. Homozygosity at the codon 129 polymorphism has a profound influence on the incidence of sporadic CJD [Palmer et al., *Nature* 352:340–342 (1991)]. The MHu2MPrP transgene encodes a Met at codon 129 and the iatrogenic CJD case was homozygous for Met [Collinge et al., *Lancet* 337:1441–1442 (1991)].

To break the species barrier we have created an artificial PrP gene which, when inserted into a host mammal (such as a mouse) renders that mammal susceptible to infection with prions which normally infect only a genetically diverse test mammal (e.g. a human, cow or sheep). The artificial PrP gene may include the natural PrP gene sequence of the host animal with one or more (preferably less than 40) codon sequences being replaced with other codon sequences such as corresponding codons of a genetically diverse mammal (e.g. a human, cow or sheep).

In a specific example of the invention the species barrier is broken by inserting into a mammal (a mouse) the chimeric gene (MHu2M) which is shown being assembled schematically in FIG. 1. In order to produce the chimeric gene, it is first necessary to obtain nucleotide sequences which encode human PrP (SEQ ID NO:2). The human PrP genes are then subjected to the conventional PCR procedures in order to produce large numbers of copies of the gene or portions of the gene. The PCR product is then isolated, specific restriction sites are added and the copied product is subjected to specific endonucleases in order to remove a middle section of the human PrP gene. Specifically, restriction sites are added such that when the PCR product is subjected to endonucleases such as Asp718 as well as BstEII, a section of the gene is cut out. The use of these two endonucleases will remove a center portion of the human PrP gene (codons 94–188) which portion encodes amino acid residues 94 through 188. Endonucleases are also used to remove a corresponding center portion of the mouse PrP gene. The removed center portion of the mouse gene is then discarded and the center portion obtained from the human PrP gene is fused into the mouse gene to produce a chimeric human/mouse gene. Details of how the specific MHu2M gene was produced are described in Example 1 and shown in FIG. 1.

Figure 2:
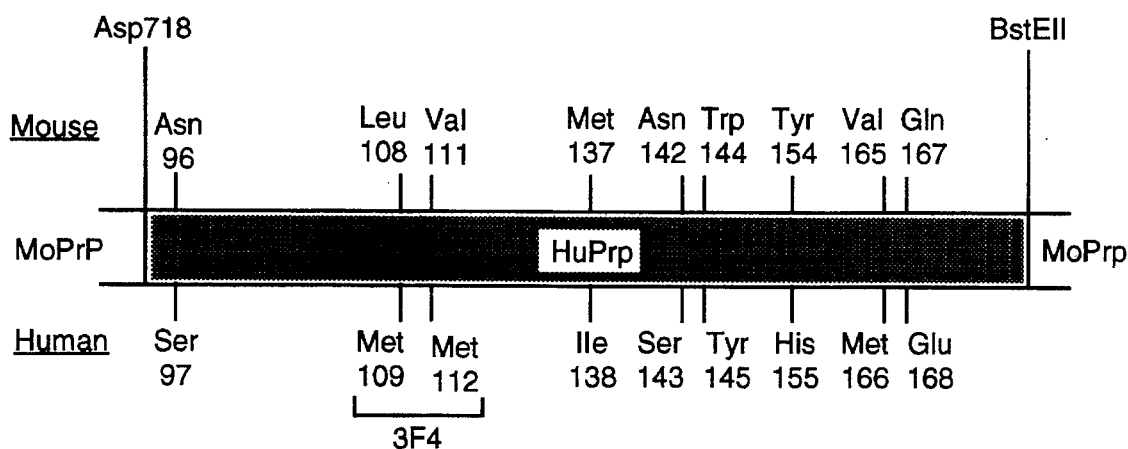
FIG. 2 is a schematic view of a portion of PrP proteins showing the differences between a normal, wild-type human PrP protein and a normal, wild-type mouse PrP protein.

As shown with FIG. 2, there is a high degree of homology between the removed center portion of the human PrP gene and the segment of the mouse PrP gene which is replaced. Specifically, the segments differ at nine codons. Thus, when the genetic material is expressed, the resulting chimeric MHu2M protein will differ from MoPrP at 9 residues. These residues and their positions are shown in FIG. 2. After the chimeric gene is produced, it can be microinjected into a mouse egg using known technology as described within Scott et al., Cell 59:847–857 (1989) and Scott et al., Protein Sci. 1:986–997 (1992) and see also WO91/19810 published Dec. 22, 1991 as well as other publications relating to the production of transgenic mice cited therein and known to those skilled in the art. The injected mouse egg is then implanted into a mouse using known procedures. Multiple eggs can be implanted into a single mouse and known procedures can be used to determine whether the resulting offspring are transgenic mice which include the chimeric gene within their genome. Details of this procedure are described in Example 1.

We have successfully broken the "species barrier" by producing a chimeric PrP gene wherein a middle portion of the mouse PrP gene is replaced with a corresponding middle portion of a human PrP gene thereby leaving the C- and N-terminus of the mouse PrP gene intact. However, other segments of the mouse PrP gene can be replaced with other homologous segments of the human PrP gene and obtain a transgenic mouse which is subject to being readily infected with human prions. Thus, the invention is not limited to the particular chimeric gene MHu2M or chimeric mice produced using this gene. The invention includes all types of transgenic animals which include artificial genes wherein the artificial gene renders the transgenic animal susceptible to infection with prions which normally infect only a genetically diverse animal. Further, the invention includes transgenic animals wherein the host animal has its genome changed to include multiple copies of the entire PrP gene of a genetically diverse test animal. Thus, for example, the invention includes transgenic mice and hamsters altered to include two fold or higher levels of expression of the PrP gene of a genetically diverse test animal such as a human, cow or sheep. The two fold or higher levels of expression can be obtained by including higher copy numbers such as 30 or more copies of the PrP gene of the genetically diverse test animal and/or by including an enhanced promoter which elevates the level of expression of even a low copy number of the gene.

Numerous specific examples of artificial genes of the invention can be deduced from reviewing FIGS. 3, 4 and 5. Specifically, one may start with the basic PrP gene of a mouse (as the host animal) which animal is to become the transgenic animal. Thereafter, one or more codons of the mouse gene may be replaced with one or more corresponding codons of a human, bovine or sheep PrP gene which codon is different from the corresponding codon of the mouse gene but at the same relative position in the gene. By showing that it is possible to break the "species barrier" by creating a particular chimeric gene whereby transgenic mice can test for the presence of human prions we have opened the door for the creation of other transgenic animals which will include other artificial PrP genes which, for example, can allow for the testing for the presence of bovine or ovine prions in a sample.

Tg(MHu2M) mice with shorter incubation times

The incubation time of Tg(MHu2M) mice inoculated with Hu prions is now about 200 days ±50 days, which can be reduced substantially by increasing the copy number of the MHu2M gene (e.g. to about 50±25) and thereby obtaining an elevated level of expression. In Tg(SHaPrP) mice, the level of SHaPrP transgene expression was found to be inversely proportional to the length of the scrapie incubation time after inoculation with SHa prions [Prusiner et al., Cell 63:673–686 (1990)]. Thus, producing Tg(MHu2M) mice with higher levels of transgene expression is a means of substantially reducing incubation time.

Based on other studies which we have performed using an analogous hamster/mouse chimeric PrP gene, MH2M, it is possible to assign a theoretical optimal incubation period for the MHu2M construct in a mouse lacking the endogenous mouse PrP gene. We obtained incubation periods of ~105 days with a heterologous Syrian hamster prion inoculum, shortening to ~62 days with a homologous MH2M prion inoculum. The shortest incubation period so far observed in any of our transgenic mouse studies was ~45 days for a line expressing the mouse PrP gene. Assuming a similar minimum incubation period with MHu2M prions in Tg(MHu2M PrP) mice lacking the endogenous mouse PrP gene, we can confidentially expect incubation periods of the order of 45×105/62=76 days with human prions. This is a conservative estimate; even shorter incubation periods can be obtained in lines with very high copy numbers. Copy numbers can be increased up to about 100 and the incubation time can be as short as 50 days ±20 days. In addition, other chimeric human/mouse PrP constructs may exhibit even shorter incubation times than MHu2M PrP. It is preferable to keep the copy number below about 100 in order to avoid producing transgenic animals which become sick without inoculation with prions.

In addition, removing MoPrP$^C$ by crossing Tg(MHu2M) mice onto an ablated background (Prn-p$^{0/0}$) may also reduce the incubation time since Tg(SHaPrP$^{+/0}$)81/Prn-p$^{0/0}$ mice exhibit a 30% reduction in incubation times compared to Tg(SHaPrP$^{+/0}$)81/Prn-p$^{+/+}$ mice [Büeler et al., Cell 73:1339–1347 (1993). Prusiner et. al., Proc. Natl. Acad. Sci. USA 90:10608–10612 Nov. 1993. Accordingly, we have also used fertilized eggs from mice in which the endogenous PrP gene has been ablated as recipients for microinjection of the MHu2M PrP construct.

By systematically altering the extent and position of the substitutions in other chimeric Hu/Mo PrP constructs, it is possible to further enhance the susceptibility of Tg mice to Hu prions as reflected by shortened incubation times. Shortening the incubation time is a worthwhile goal for the facilitation of many future studies in prion research and for the evaluation of pharmaceuticals, foods, tissues, organs, grafts, cosmetics and other substances—particularly substances which have some portion derived from an animal, such as a human, which animal might be infected with prions.

In general, there is an inverse relationship between the number of copies of a chimeric or artificial PrP gene and the incubation time of disease after inoculation of the transgenic animal with prions. Specific MHu2M mice disclosed herein have only 3 or 4 copies of the MHu2M gene. The number of copies can be increased to 30 to 400, thereby significantly reducing the incubation time from about 200 days to 50 days ±20 days or less.

Pathogenic mutations and polymorphisms

There are a number of known pathogenic mutations in the human PrP gene. Further, there are known polymorphisms in the human, sheep and bovine PrP genes. The following is a list of such mutations and polymorphisms:

| Pathogenic human mutations | Human Polymorphisms | Sheep Polymorphisms | Bovine Polymorphisms |
| --- | --- | --- | --- |
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro—Leu | | | |
| Codon 105 Pro—Leu | | | |
| Codon 117 Ala—Val | | | |
| Codon 145 Stop | | | |
| Codon 178 Asp—Asn | | | |
| Codon 180 Val—Ile | | | |
| Codon 198 Phe—Ser | | | |
| Codon 200 Glu—Lys | | | |
| Codon 210 Val—Ile | | | |
| Codon 217 Asn—Arg | | | |
| Codon 232 Met—Ala | | | |

The DNA sequence of the human, sheep and cow PrP genes have been determined allowing, in each case, the prediction of the complete amino acid sequence of their respective prion proteins. The normal amino acid sequence which occurs in the vast majority of individuals is referred to as the wild-type PrP sequence. This wild-type sequence is subject to certain characteristic polymorphic variations. In the case of human PrP (SEQ ID NO:2), two polymorphic amino acids occur at residues 129 (Met/Val) and 219 (Glu/Lys). Sheep PrP (SEQ ID NO:4) has two amino acid polymorphisms at residues 171 and 136, while bovine PrP (SEQ ID NO:3) has either five or six repeats of an eight amino acid motif sequence in the amino terminal region of the mature prion protein. While none of these polymorphisms are of themselves pathogenic, they appear to influence prion diseases. Distinct from these normal variations of the wild-type prion proteins, certain mutations of the human PrP gene which alter either specific amino acid residues of PrP or the number of octarepeats have been identified which segregate with inherited human prion diseases.

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., *Proc. Natl. Acad. Sci. USA* 89:9097–9101 (1992). The sequence for the Syrian hamster is published in Basler et al., *Cell* 46:417–428 (1986). The PrP gene of sheep is published by Goldmann et al., *Proc. Natl. Acad. Sci. USA* 87:2476–2480 (1990). The PrP gene sequence for bovine is published in Goldmann et al., *J. Gen. Virol.* 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). These publications are all incorporated herein by reference to disclose and describe the PrP gene and PrP amino acid sequences.

Differences in the conversion of MHu2MPrP$^C$ and HuPrP$^C$ into the scrapie isoform in mice The fundamental event in prion propagation seems to be the conversion of PrP$^C$, which contains ~43% α-helix and is devoid of β-sheet, into PrP$^{Sc}$ which has ~43% β-sheet [Pan et al., *Proc. Natl. Acad. Sci. USA* 90:10962–10966 (1993)]. From the results of Tg(SHaPrP) mouse studies, this process is thought to involve the formation of a complex between PrP$^{Sc}$ and the homotypic substrate PrP$^C$ [Prusiner et al., *Cell* 63:673–686 (1990)]. Attempts to mix PrP$^{Sc}$ with PrP$^C$ have failed to produce nascent PrP$^{Sc}$ [Raeber et al., *J. Virol.* 66:6155–6163 (1992)], raising the possibility that proteins such as chaperones might be involved in catalyzing the conformational changes that feature in the formation of PrP$^{Sc}$. One explanation for the difference in susceptibility of Tg(MHu2M) and Tg(HuPrP) mice to Hu prions in mice may be that mouse chaperones catalyzing the refolding of PrP$^C$ into PrP$^{Sc}$ can recognize MHu2MPrP but not HuPrP.

Another possibility is that sequences at the N- or C-terminus of HuPrP inhibit the formation of PrP$^{Sc}$ in murine cells. To test this possibility, HuPrP sequences are substituted for the Mo sequences at each terminus of MHu2MPrP. Comparison of the PrP sequences in many mammals around the GPI anchor addition site (codons 227–235) reveals an interesting difference of four amino acids between rodents and primates [Stahl et al., *Biochemistry* 31:5043–5053 (1992)]. In support of this hypothesis is that rodents also differ from ruminants including sheep and cattle at this site; sheep prions have failed to transmit neurodegeneration to Tg(ShePrP). In these experiments the transgenic mice expressed the entire sheep PrP gene.

In contrast to Tg(MHu2M) mice, the overall transmission rate of Hu prion inocula from a wide variety of sources was less than 10% in Tg(HuPrP) mice, no different from the rate observed in non-Tg mice. Likewise the conversion of HuPrP$^C$ into HuPrP$^{Sc}$ in Tg(HuPrP) mice appears to be a relatively infrequent event similar to the rare conversion of MoPrP$^C$ to PrP$^{Sc}$ in response to human prions. The low rates of transmission in these mice do not seem to be a consequence of low titers of human prion titers: two inocula which failed to cause disease in Tg(HuPrP) mice transmitted to 100% of inoculated Tg(MHu2M) animals.

"Strains" of human prions

Studies in rodents have shown that prion strains produce different patterns of PrP$^{Sc}$ accumulation [Hecker et al., *Genes& Development* 6:1213–1228 (1992); DeArmond et al., *Proc, Natl. Acad. Sci. USA* 90:6449–6453 (1993)]; which can be dramatically changed by the sequence of PrP$^C$ [Carlson et al., *Proc. Natl. Acad. Sci. USA* in press (1994)]. The molecular basis of prion diversity has for many years been attributed to a scrapie specific nucleic acid [Bruce et al., *J. Gen. Virol.* 68:79–89 (1987)] but none has been found [Meyer et al., *J. Gen. Virol.* 72:37–49 (1991); Kellings et al., *J. Gen. Virol.* 73:1025–1029 (1992)]. Other hypotheses to explain prion strains include variations in PrP Asn-linked sugar chains [Hecker et al., *Genes & Development*

6:1213–1228 (1992)] and multiple conformers of PrP$^{Sc}$ [Prusiner, S.B., Science 252:1515–1522 (1991)]. The patterns of PrP$^{Sc}$ in Tg(MHu2M) mice were remarkably similar for the three inocula from humans dying of CJD.

The patterns of PrP$^{Sc}$ accumulation in the brains of inoculated Tg(MHu2M) mice were markedly different for RML prions and Hu prions. However, RML prion inocula containing MoPrP$^{Sc}$ stimulated the formation of more MoPrP$^{Sc}$ while Hu prion inocula containing HuPrP$^{CJD}$ triggered production of MHu2MPrP$^{Sc}$. The distribution of neuropathological changes characterized by neuronal vacuolation and astrocytic gliosis is similar to the patterns of PrP$^{Sc}$ accumulation in the brains of Tg(MHu2M) mice inoculated with RML prions or Hu prions.

New approaches to investigating human prion diseases

The remarkable sensitivity of Tg(MHu2M) mice to Hu prions represents an important advance in neurodegenerative disease research. Based on the present disclosure regarding chimeric Hu/Mo PrP transgenes we conceived of a similar approach to the construction of Tg mice susceptible to BSE and scrapie sheep prions. Such would be useful in detecting prion diseases in domestic animals. The importance of animal prion diseases is illustrated by BSE or "mad cow disease" in Great Britain, where >150,000 cattle have died. This prion disease BSE is thought to have originated with cattle consuming meat and bone meal produced from sheep offal containing scrapie prions [Wilesmith, J. W., Semin. Viro. 2:239–245].

The BSE epidemic has led to considerable concern about the safety for humans of European beef and other cattle products. Epidemiologic studies over the past two decades have provided much data arguing that humans are unlikely to contract CJD from scrapie-infected sheep products [Harries-Jones et al., J. Neurol. Neurosurg. Psychiatry 51:1113–1119 (1988); Cousens et al., J. Neurol. Neurosurg. Psychiatry 53:459–465 (1990); Brown et al., Neurology 37:895–904 (1987)]. There are seven amino acid substitutions which distinguish bovine from sheep PrP which must be considered in drawing conclusions from sheep scrapie about the risk factors to humans from BSE. Whether any of these seven amino acid substitutions render bovine prions permissive in humans remains to be established. It may be that Tg(MHu2M) mice are susceptible to bovine as well as sheep prions. Of perhaps even greater importance, Tg(MHu2M) mice have immediate application in the testing of pharmaceuticals for human prion contamination. The Tg(MHu2M) mice described here provide a sensitive, reliable and economical bioassay for detecting the presence of human prions.

Chimeric PrP Gene

Since the fundamental event underlying prion propagation seems to be a conformational change in PrP [Pan et al., Proc. Natl. Acad. Sci, USA 90:10962–10966 (1993)] and mouse PrP differs from human PrP at 31 positions out of 254 [Kretzschmar et al., DNA 5:315–324 (1986)], we constructed modified PrP transgenes. Chimeric SHa/Mo transgenes have produced prions with new properties, the most useful being the chimeric SHa/Mo transgene labeled MH2M which carries 5 amino acid substitutions found in SHaPrP lying between codons 94 and 188. [Scott et al., Cell 73:979–988 (1993)]. We made an analogous chimeric human/mouse PrP gene, which we call MHu2M, in which the same region of the mouse gene is replaced by the corresponding human sequence which differs from mouse PrP at 9 codons as is shown in FIG. 2.

We have found that mice expressing the MHu2M chimeric transgene are susceptible to human prions after abbreviated incubation times. More specifically, the transgenic mice of the present invention which include the chimeric MHu2M gene will, after inoculation with human prions, develop disease symptoms attributed to the prions within about 200 days ±50 days. Further, 80% or more the transgenic mice of the invention inoculated with human prions will develop symptoms of the disease, more preferably 98% or more of the mice will develop symptoms of the disease. According to experiments carried out, 100% of the transgenic MHu2M mice inoculated with human prions actually developed symptoms of the disease in about 200 days ±50 days.

These findings indicate that murine cells cannot readily convert HuPrP$^C$ into HuPrP$^{Sc}$ but they can process MHu2MPrP$^C$ into MHu2MPrP$^{Sc}$. Since Tg(MHu2M) mice develop neurodegeneration more rapidly than monkeys, they provide a preferred host for bioassays of infectivity in tissues of humans dying of prion diseases. The Tg(MHu2M) mice disclosed herein provide an excellent system for assessing the sterility of pharmaceuticals as well as tissue and organ grafts prepared from human sources. Other transgenic mice which include the prion protein gene of the animal in danger of infection can be used to test samples for prion diseases which can infect domestic animals such as sheep and cattle.

Samples for assay may be obtained from any source, including animal and plant sources. Such samples are prepared for innoculation into the transgenic mammal by the methods described herein or methods known to those skilled in the art.

Chimeric MHu2M gene

FIG. 1 is shown regarding how to create the chimeric MHu2M gene. At first, we engineered a new KpnI site in the HuPrP ORF cassette (shown shaded), changing nucleotide 282 from a cytosine to a thymine residue by PCR-mediated mutagenesis. This mutagenic change conserves the amino acid sequence of HuPrP. A second oligonucleotide primer complimentary to DNA sequences around the BstEII-cut product was used to replace the corresponding MoPrP gene fragment (the MoPrP gene is unshaded) creating the hybrid gene MHu2M. Microinjection of a cosSHa.Tet construct bearing this expression cassette resulted in founder animal Tg(MHu2M)FVB-B5378.

An expanded representation of the region of MHu2MPrP between codons 94 and 188 which is flanked by MoPrP (SEQ ID NO:1) sequences (FIG. 2). MHu2MPrP differs from MoPrP by nine amino acids in the region between amino acids 96 and 167. These amino acid residues which are derived from HuPrP (SEQ ID NO:2) are shown on the lower section of the diagram; the amino acids at the same position of MoPrP (SEQ ID NO:1) are shown above. The discrepancy of amino acid positions is due to MoPrP (SEQ ID NO:1) having one less amino acid than HuPrP (SEQ ID NO:2) in the region immediately upstream from the replacement.

Artificial PrP Genes

The real power of the present invention lies in the understanding that a variety of different artificial PrP genes can be created which, when inserted into a host animal, will render that animal susceptible to infection with prions which normally only infect a second and genetically diverse test animal. There are nearly an infinite number of possible artificial PrP genes which would meet the basic criteria of the invention, i.e. rendering a mammal such as a mouse susceptible to infection with prions which normally infect only a genetically diverse test animal such as a human. The MHu2M gene of the invention is only one specific example of an artificial gene which achieves the primary object of the invention. By reviewing FIGS. 3, 4 and 5 numerous other artificial gene possibilities will be deduced by those skilled in the art. Specifically, referring to FIG. 3 one can readily determine the amino acid sequence of mouse PrP (SEQ ID NO:1) and observe the positions wherein the mouse PrP (SEQ ID NO:2) sequence differs with a human PrP sequence. Thus, to create an artificial gene one can substitute a codon (or sequence of codons) of a mouse PrP gene with a codon (or sequence of codons) of a human PrP gene at the same position which will encode a different amino acid— any (but not all) of the codons where different sequences appear can be used for substitution, It will be understood by those skilled in the art that, if all of the codons where differences appear between the mouse and the human were substituted, the resulting gene would be the human PrP gene, which is not part of the present invention. However, as explained above, the entire human PrP gene can be inserted into a host animal such as a mouse to create a transgenic animal of the invention, expressing two fold or higher levels of human $PrP^C$ are included. Transgenic mice expressing only low levels of human $PrP^C$ are unlikely to become ill after inoculation with human prions. However, if the level of human $PrP^C$ expression is elevated, the transgenic animals become susceptible to infection with human prions. This is another means of overcoming the species barrier by what is referred to as a stochastic process.

Referring to FIG. 4 it can be seen how it would be possible to produce artificial PrP genes wherein the resulting gene could be inserted into a mouse in order to render the mouse susceptible to infection with bovine prions. A similar strategy with respect to producing a mouse which would be susceptible to infection with sheep prions can be deduced from reviewing FIG. 5. In addition to these possibilities those skilled in the art will recognize that, in certain instances, completely artificial nucleotide sequences can be used as corresponding substitutes for a portion of the natural sequence in order to obtain a useful artificial gene which, when inserted into an animal, will render that animal susceptible to infection with prions which normally would infect only a genetically diverse mammal.

Other artificial genes of the invention include genes which may be native or artificial and are operatively fused to an enhanced promoter such as a neuronal enolased promoter. The enhanced promoter is such that when inserted into the host mammal will express the PrP gene at a level sufficiently high to render the host animal susceptible to infection with prions which normally only infect a genetically diverse test animal.

Evidence of Disease $PrP^{Sc}$ has been found in the brains of affected Tg(MHu2M) mice after inoculation with Hu(CJD) or Mo(RML) prions. Brain homogenates of Tg(MHu2M) were either left undigested or digested with proteinase K (BMB) at a final concentration of 20 µg/ml for 1 hour at 37° C. (even numbered lanes). Samples were resolved by SDSPAGE and then analyzed by Western blot.

The distribution of $PrP^C$ and $PrP^{Sc}$ in clinically sick Tg(MHu2M) mice inoculated with Mo(RML) and Hu(CJD) prions were detected by the histoblot method. The histoblots included those of coronal sections through the region of the hippocampus and thalamus. Differences are observed between: (A) $PrP^C$ in Mo(RML) infected mouse; (B) $PrP^C$ in sporadic CJD RG-infected mouse; (C) $PrP^{Sc}$ in Mo(RML) infected mouse; (D) $PrP^{Sc}$ in sporadic CJD RG-infected mouse; (E) $PrP^{Sc}$ in sporadic CJD EC-infected mouse; and (F) $PrP^{Sc}$ in iatrogenic CJD (#364)-infected mouse.

EXAMPLES

The following examples are put forth so as to provide those of ordinary skill in the art with a complete disclosure and description of how to make and use the chimeric genes, transgenic mice and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Chimeric gene (MHu2M)

The source of the HuPrP ORF for construction of an expression cassette has been described [Hsiao et al., *Nature* 338:342–345 (1989)]. The construction of the MHu2M gene is described in connection with the description of FIG. 1. All PrP ORF cassettes were flanked by SalI and XhoI, which cleave immediately adjacent to the PrP initiation and termination codons of the PrP ORF respectively, allowing for convenient subcloning into the cos.SHaTet cosmid expression vector [Scott et al., *Cell* 73:979–988 (1993)]. The isolation and screening of recombinant cosmid clones was achieved by methods which have been previously described [Scott et al., *Cell* 73:979–988 (1993)].

Example 2

Producing Transgenic Mice/Tg(MHu2M).

The nucleotide sequences of the HuPrP and MHu2MPrP ORFs of Example 1 were verified. The cosmid NotI fragments, recovered from large-scale DNA preparations, were used for microinjection into the pronuclei of fertilized C57BL/6 × SJL or FVB/N oocytes as previously described [Scott et al., *Cell* 59:847–857 (1989); Scott et al., *Protein Sci.* 1:986–997 (1992)]. Genomic DNA isolated from tail tissue of weaning animals was screened for the presence of incorporated transgenes using a probe that hybridizes to the 3'-untranslated region of the SHaPrP gene contained in the cosSHa.Tet vector [Scott et al., *Protein Sci.* 1:986–997 (1992)]. The offspring obtained were tested and it was confirmed that the chimeric MHu2M gene was integrated into the genome of these offspring. As shown in Example 5 below, these mice were found to be susceptible to infection with human prions 100% of the time.

Example 3.

Preparation of brain homogenates

A 10% [w/v] homogenate of a sample of thawed human brain tissue was prepared in phosphate buffered saline lacking calcium and magnesium ions. The tissue was initially dissociated using a sterile disposable homogenizer, and this suspension was subjected to repeated extrusion through an 18 gauge syringe needle followed by a 22 gauge needle. Samples for inoculation into test animals were diluted 10-fold. Homogenates of clinically sick Tg and non-Tg mouse brains were prepared in the same way except for the omission of the initial dissociation step.

Example 4

Sources of prion inocula

Human inocula were derived from frozen brain tissues of patients in which the clinical diagnosis of CJD or GSS had been confirmed by histopathological examination of brain tissues and, in most cases, by prion protein analysis. In some cases, the PrP gene was amplified by PCR of DNA isolated from patient blood and the PrP sequence determined by DNA sequence analysis. No HuPrP mutations were detected in cases of sporadic or iatrogenic CJD. The RML isolate was obtained from Swiss mice [Chandler, R. L., *Lancet*

1:1378–1379 (1961)] from a closed colony at the Rocky Mountain Laboratory or in Swiss CD-1 mice obtained from Charles River Laboratories.

Example 5

Determination of Scrapie Incubation Periods

Transgenic mice as per Example 2 were inoculated intracerebrally with 30 μl of brain extract using a 27 gauge needle inserted into the right parietal lobe. The preparation of inocula and criteria for diagnosis of scrapie in mice have been described [Carlson et al., *Cell* 46:503–511 (1986)]. Beginning 50 days after inoculation, the mice were examined for neurologic dysfunction every 3 days. When clinical signs of scrapie appeared, the mice were examined daily. When some animals whose death was obviously imminent were identified, their brains were taken for histopathologic studies (as per the procedures of Example 3) and confirmation of the diagnosis of scrapie.

Example 6

Immunoblot Analysis

For the determination of the relative levels of PrP expression in Tg mouse and human brains, protein concentrations were determined by bicinchoninic acid assay and immuno dot blots as previously described [Scott et al., *Cell* 73:979–988 (1993)]. Samples for Western blot analysis were prepared and Western blots were performed as described previously [Towbin et al., *Proc. Natl. Acad. Sci. USA* 76:4350–4354 (1979)], except that an enhanced chemiluminescent (ECL) detection method (Amersham) was used. The blot was exposed to X-ray film for 5–60 seconds. α-PrP RO73 rabbit antiserum was used at a final dilution of 1:5000 and 3F4 monoclonal antibody was also employed [Serban et al., *Neurology* 40:110–117 (1990)].

Example 7

Tg(MHu2MPrP) Mice Are Susceptible to Human Prions

Using information from a systematic study of chimeric SHa/Mo PrP genes, a chimeric Hu/Mo PrP gene analogous to MH2M was constructed as per Example 1. This gene, which we call MHu2M, differs from MoPrP at 9 positions, all of which lie between codons 94 and 188 as is shown in FIG. 2. A Tg mouse was constructed expressing the MHu2M PrP gene and the founder designated Tg(MHu2M)FVB-B5378 as per Example 2. By serial dilution of Tg(MHu2M) mouse and human brain homogenates, we estimate that the level of $MHu2MPrP^{C}$ in the brains of these Tg(MHu2M)FVB-B5378 mice are similar to those of $HuPrP^{C}$ found in human brain using an immuno dot blotting procedure.

Tg(MHu2M) mice as per Example 2 were inoculated with brain homogenates from three unrelated Caucasian patients who had died of CJD. Two of the three patients died of sporadic CJD: one (R.G.) was a 56-year-old American female; the other (E.C.) was a 61-year-old Canadian female. In both cases, cerebrocortical biopsy showed severe spongiform degeneration. The third (#364) was a British youth who had contracted iatrogenic CJD after treatment for hypopituitarism with human growth hormone (HGH) derived from cadaveric pituitaries [Collinge et al., *Lancet* 337:1441–1442 (1991)]. Brain homogenates from all three CJD patients exhibited protease-resistant PrP by Western immunoblotting. This protease-resistant isoform of PrP is designated $PrP^{Sc}$, or often $PrP^{CJD}$ when it is found in humans.

All of the Tg(MHu2M) mice inoculated with homogenates from the CJD patients described above developed signs of central nervous system (CNS) dysfunction ~200 days after inoculation (see Table 1 below). The clinical signs were similar to those of murine scrapie. After developing clinical signs, the inoculated Tg(MHu2M) mice died rapidly, often within a day. Two of the eight uninoculated Tg(MHu2M) mice are now >500 days of age and remain well; the youngest of the other six uninoculated animals is older than the age at which inoculated Tg(MHu2M) mice developed signs of CNS dysfunction.

Inoculation of Tg(MHu2M) mice with Mo(RML) prions passaged in mice produced disease in 178±3 days, which is ~40 longer than Mo(RML) prions in non-Tg mice. Prolongation of incubation times in mice expressing non-murine transgenes is well established, and occurs presumably because the foreign $PrP^{C}$ molecule inhibits the conversion of $MoPrP^{C}$ into $MoPrP^{Sc}$ [Prusiner et al., *Cell* 63:673–686 (1990)]. In contrast to Tg(MHu2M) mice, incubation times for RML prions in Tg(MH2M) mice were the same as those of the non-Tg mice [Scott et al., *Cell* 73:979–988 (1993)].

TABLE 1

| | Incubation of human (CJD) and mouse (RML) prion inocula in Tg(MHu2M)FVB-B5378 mice Incubation Times (mean days ± SE) | | | | |
|---|---|---|---|---|---|
| Source | Inoculum | No.[a] | Range (days) | Illness | Death[b] |
| Sporadic CJD | RG | 8/8 | 225–249 | 238 ± 3.2 | 240 ± 5.4(3) |
| Sporadic CJD | EC | 7/7 | 202–229 | 218 ± 4.6 | N.D. |
| Iatrogenic CJD | #364 | 9/9 | 221–245 | 232 ± 2.9 | 235 ± 3.9(5) |
| Mo | RML | 19/19 | 155–195 | 178 ± 3.3 | 203 ± 2.0(14) |

[a]Number of animals developing clinical sickness (neurological dysfunction) divided by the total number of animals inoculated. In the case of inoculum RG, three animals were found dead after 224, 238, and 243 days before a clinical diagnosis could be made. In the case of inoculum EC, two animals were found dead after 225 and 226 days before a clinical diagnosis could be made. In each case, these animals died at the same time that clinical diagnosis was made in other inoculated animals.
[b]The number of mice dying of scrapie is shown in parentheses. Mice sacrificed for pathological examination are excluded from these calculations.

Example 8

Comparative Example

Tg(HuPrP) Mice Are Resistant to Human Prions

Tg mice expressing HuPrP (SEQ ID NO:2) were produced using the HuPrP gene ORF, which had been cloned into the cosSHa. Tet expression vector [Scott et al., *Protein Sci.* 1:986–997 (1992)]. Microinjection of outbred C57B6/SJL and inbred FVB mouse embryos resulted in two founder transgenic animals designated Tg(HuPrP)B6SJL-110 and Tg(HuPrP)FVB-152. We estimated by serial dilution of brain homogenates and immuno dot blotting, that the level of $PrP^C$ in the brains of the progeny of these founders express HuPrP (SEQ ID NO:2) at levels 4- to 8-fold higher than the level of HuPrP (SEQ ID NO:2) found in the human brain.

To determine whether expression of HuPrP (SEQ ID NO:2) in Tg(HuPrP)B6SJL-110 and Tg(HuPrP)FVB-152 conferred susceptibility to human prions, incubation periods were measured after inoculation of Tg(HuPrP) and non-Tg mice with brain extracts from 18 patients that had died of sporadic CJD, iatrogenic CJD, familial CJD or GSS. From experiments performed over the past 2.5 years, we concluded that the two lines of Tg(HuPrP) mice were no more responsive than non-Tg mice to human prions (see Table 2 below). The rate of transmission to Tg(HuPrP) mice was 8.3% (14 clinically sick mice out of 169 mice) which was similar to a transmission rate of 10.3% in control non-Tg mice (6 clinically sick mice out of 58 mice). In the infrequent event of a positive transmission, incubation times were extremely long ranging, from 590 days to 840 days in both Tg(HuPrP) and non-Tg mice. By this late time, many animals had died of intercurrent illnesses which complicated diagnosis. The difficulty of interpreting transmissions occurring after extremely long incubation periods is compounded by the heightened potential for artifactual results due to low levels of contaminating prions.

Statistical analysis shows that the frequency of Hu prion transmission to Tg(MHu2MPrP) mice compared to Tg(HuPrP) and non-Tg mice is highly significant using the Fisher's exact test, $p<10^{-7}$ [Mehta et al., *J. Am. Stat. Assn.* 78:(392) 427–434 (1983)]. When Hu prion transmission to Tg(HuPrP) mice was compared to non-Tg mice, the frequencies were similar, $p=0.79$.

To confirm the clinical diagnosis of prion disease, 5 ill Tg(HuPrP) and 1 non-Tg mice were sacrificed and brain extracts were examined for the presence of $PrP^{Sc}$ by Western blotting with the α-PrP antibodies, 3F4 mAb and RO73 antiserum [Kascsak et al., *J. Virol.* 61:3688–3693 (1987); Serban et al., *Neurology* 40:110–117 (1990)]. The 3F4 mAb reacts specifically with HuPrP (SEQ ID NO:2) allowing discrimination from MoPrP (SEQ ID NO:1). $MoPrP^{Sc}$ was detected in the brain of the non-Tg mouse inoculated with sporadic CJD inoculum #87011 which developed clinical signs after 756 days, while 3F4-reactive $PrP^{Sc}$ was detected in the brains of two Tg(HuPrP) mice which developed clinical signs after 589 days post-inoculation with iatrogenic CJD inoculum #170. The equivalent transmission rates of human prions in Tg(HuPrP) and non-Tg mice indicate that this is a rare event with the same frequency of occurrence as the stochastic conversion of $MoPrP^C$ to $MoPrP^{Sc}$ induced by human prions.

The absence of either RO73- or 3F4-reactive $PrP^{Sc}$ in the brains of 3 out of the 6 mice analyzed may reflect the difficulty of accurately diagnosing prion disease in elderly animals. Some of the mice inherited prion diseases of both humans and Tg mice exhibit little or undetectable levels of protease-resistant PrP; yet, based on transmission studies, their brains contain prions and they show clear spongiform degeneration [Medori et al., *N. Engl. J. Med.* 326:444–449 (1992)].

In contrast to Tg(MHu2M) mice, Hu prions from patient RG have not transmitted to either Tg(HuPrP) or non-Tg mice after >330 days (see Table 2 below). Attempts to transmit preparations enriched for Hu prion rods prepared from the brain of patient RG have likewise been negative for >300 days. In addition, inoculum from the iatrogenic CJD case (#364) has produced illness in neither Tg(HuPrP) nor non-Tg mice after >780 days (as shown in Table 2 below).

TABLE 2

Incubation times in Tg(HuPrP)FVB-152 and Tg(HuPrP) B6SJL-110 mice after inoculation with brain extracts from patients with human prion diseases

| Host | Inoculum | $(n/n_o)^a$ | Incubation times (days ± SE)$^b$ |
|---|---|---|---|
| Tg 152 | Sporadic CJD (#87011) | 1/10 | 706 |
| Non-Tg | Sporadic CJD (#87011) | 3/5 | 697.3 ± 5 |
| Tg 152 | Sporadic CJD (#88037) | 3/10 | 680 ± 28 |
| Tg 152 | Sporadic CJD (RG) | 0/10 | |
| Non-Tg | Sporadic CJD (RG) | 0/10 | |
| Tg 152 | Sporadic (RG) Rods | 0/8 | |
| Non-Tg | Sporadic (RG) Rods | 0/8 | |
| Tg 152 | Codon 102 GSS (#87027) | 4/10 | 724 ± 16 |
| Non-Tg | Codon 102 GSS (#87027) | 0/10 | 679 |
| Tg 152 | Codon 102 GSS (#87031) | 0/10 | |
| Non-Tg | Codon 102 GSS (#87031) | 1/5 | 742 |
| Tg 152 | Codon 178 F-CJD | 0/8 | |
| Non-Tg | Codon 178 F-CJD | 0/8 | |
| Tg 110 | Sporadic CJD (#87036) | 0/8 | |
| Non-Tg | Sporadic CJD (#87036) | 1/5 | 838 |
| Tg 110 | Iatrogenic CJD (#703) | 0/10 | |
| Non-Tg | Iatrogenic CJD (#703) | 0/5 | |
| Tg 110 | Iatrogenic CJD (#170) | 2/10 | 589 ± 0 |
| Non-Tg | Iatrogenic CJD (#170) | 0/5 | |
| Tg 110 | Iatrogenic CJD (#364) | 0/10 | |
| Non-Tg | Iatrogenic | 0/5 | |

TABLE 2-continued

Incubation times in Tg(HuPrP)FVB-152 and Tg(HuPrP) B6SJL-110 mice after inoculation with brain extracts from patients with human prion diseases

| Host | Inoculum | $(n/n_o)^a$ | Incubation times (days ± SE)[b] |
|---|---|---|---|
| Tg 110 | CJD (#364) Codon 200 | 1/8 | 791 |
| Tg 110 | F-CJD Codon 217 | 1/8 | 874 |
| Tg 110 | GSS Codon 102 | 0/10 | |
| Tg 110 | GSS-A Codon 102 | 1/8 | 694 |
| Tg 110 | GSS-B Codon 117 GSS | 0/8 | |

[a]Number of animals developing clinical sickness divided by the total number of animals inoculated.
[b]Refers to time to diagnosis of illness.
Patients from which inoculum were derived are described in the following publications: [Collinge et al., Lancet 337: 1441–1442 (1991); Hsiao et al., Nature 8: 342–345 (1989); Hsiao et al., Neurology 41: 681–684 (1991)].

Example 9

Formation of MHu2MPrP$^{Sc}$ or MoPrP$^{Sc}$ In the Brains of Tg(MHu2M) Mice Some clinically sick Tg(MHu2M) mice inoculated with each of the three CJD prion inocula or RML prions were sacrificed for histopathological verification of disease and for prion protein analysis. Western blots of brain homogenates from Tg(MHu2M) mice infected with Hu prions probed with RO73 and 3F4 α-PrP antibodies revealed the presence of protease-resistant PrP$^{Sc}$ which reacted with the 3F4 monoclonal antibody showing this protease-resistant product to be MHu2M PrP$^{Sc}$. The epitope recognized by this antibody consists of a pair of methionine residues at positions 109 and 112 in PrP [Rogers et al., *J. Immunol.* 147:3568–3574 (1991)] which are contained in MHu2M but not in MoPrP (SEQ ID NO:1) as can be seen by the mouse/human comparison of FIG. 2. The polyclonal rabbit α-PrP antiserum RO73 diluted 1:5000 was poorly reactive with MHu2MPrP$^{Sc}$ as well as HuPrP$^C$ and HuPrP$^{Sc}$ from diseased human brains. Brain homogenates from Tg(MHu2M) mice infected with RML prions contained PrP$^{Sc}$ which was detectable only with RO73 and not 3F4 α-PrP antibodies, indicating that Tg(MHu2M) mice are capable of producing MoPrP$^{Sc}$ but not MHu2MPrP$^{Sc}$ in response to RML prions previously passaged in mice. While these findings are similar to those reported for Tg(SHaPrP) mice [Scott et al., *Cell* 59:847–857 (1989)], they contrast with those found for Tg(MH2MPrP) mice where MH2MPrP$^{Sc}$ was formed in response to RML prions [Scott et al., *Cell* 73:979–988 (1993)].

Example 10

Regional Distribution of PrP$^{Sc}$ and Patterns Of Neuropatholoqy

The distribution of Mo and MHu2M PrP$^C$ and PrP$^{Sc}$ is shown in histoblots of coronal brain sections through the hippocampus and thalamus of Tg(MHu2M) mice inoculated with RML or CJD prions. The weak immunoreactivity of MHu2M PrP with RO73 permitted a degree of analysis which had not been previously possible in Tg mice expressing SHaPrP or MH2MPrP because these PrP species react with this antibody. The pattern of PrP$^{Sc}$ deposition was highly dependent upon the species of origin of the infectious prions. When inoculated with RML prions, histoblots of the brains of Tg(MHu2M) were similar to those of CD-1 mice infected with RML prions, revealing a diffuse pattern of MoPrP$^{Sc}$ deposition in the hippocampus, thalamus, hypothalamus and all layers of the neocortex. The histoblot pattern of was strikingly different for Tg(MHu2M) mice inoculated with CJD prions. The deposition of MHu2MPrP$^{Sc}$ was confined primarily to the deep layers of the neocortex, the thalamus, particularly the ventral posterior medial thalamic nucleus, the hypothalamus and the putamen. The hippocampal region and the outer layers of the neocortex were spared. Interestingly, while the hippocampus was completely devoid of MHu2MPrP$^{Sc}$, this region showed the most intense MHu2MPrP$^C$ signal. The same pattern of MHu2MPrP$^{Sc}$ deposition was consistently observed in histoblots of Tg(MHu2M) mice inoculated with all three CJD prion isolates prepared from human brain. It is noteworthy that the pattern of MHu2MPrP$^{Sc}$ deposition is similar to the pattern of PrP$^{CJD}$ deposition observed in histoblots of the brain from which inoculum RG was derived [Taraboulos et al., *Proc. Natl. Acad, Sci. USA* 89:7620–7624 (1992)]. The spongiform degeneration in the brains of Tg(MHu2M) mice infected with Mo(RML) and Hu(CJD) prions reflected the patterns of PrP$^{Sc}$ accumulation described above.

The instant invention is shown and described herein in what is considered to be a most practical and preferred embodiments. It is recognized, however, that departures may be made from which are within the scope of the invention and that modifications will occur to one who is skilled in the art upon reading this disclosure.

We claim:

1. A transgenic mouse having a genome comprised of a PrP transgene rendering the mouse susceptible to infection with prions which infect and cause disease in a human;
   wherein the PrP transgene is comprised of a native mouse PrP gene that has one or more, but not all, of its codons that differ from a human PrP gene replaced with a corresponding human PrP gene codon;
   and further wherein said transgenic mouse exhibits symptoms of prion disease within 200 days or less after inoculation with a prion that infects and causes prion disease in humans.

2. The transgenic mouse of claim 1, wherein the Prp transgene is MHu2M.

3. A method of testing a sample for the presence of prions which infect and cause disease in a human, comprising;
   inoculating a transgenic mouse with a sample to be tested, wherein the transgenic mouse has a genome comprised of a PrP transgene rendering the mouse susceptible to infection with prions which infect and cause disease in a human, wherein the PrP transgene is comprised of a native mouse PrP gene that has one or more, but not all, of its codons that differ from a human PrP gene replaced with a corresponding human PrP gene codon, and further wherein said transgenic mouse exhibits symptoms of prion disease within 200 days or less after inoculation with a prion that infects and causes prion disease in humans;
   observing the transgenic mouse over time; and
   determining if the transgenic mouse develops symptoms of prion disease within 200 days or less after inoculation with said sample;
   wherein the presence of prions in the sample is determined if the mouse develops symptoms of prion disease and the absence of prions in the sample is determined if the mouse does not develop symptoms of prion disease.

4. The method of claim 3 wherein the sample comprises a pharmaceutically acceptable carrier.

5. The method of claim 3 wherein the sample comprises material from a human source.

6. A method of determining the efficacy of a compound for treating a disease caused by infection with human prions, comprising:
   inoculating a transgenic mouse with human prions wherein the transgenic mouse has a genome comprised of a PrP transgene rendering the mouse susceptible to infection with prions which infect and cause disease in a human, wherein the PrP transgene is comprised of a native mouse PrP gene that has one or more, but not all, of its codons that differ from a human PrP gene replaced with a corresponding human PrP gene codon, and further wherein said transgenic mouse exhibits symptoms of prion disease within 200 days or less after inoculation with a prion that infects and causes prion disease in humans;
   administering the compound to the inoculated transgenic mouse;
   observing the transgenic mouse over a period of time; and
   wherein the efficacy of the compound in treating disease caused by prions is determined by observing the mouse for symptoms of prion disease.

7. An artificial PrP gene that when inserted into the genome of a host mammal selected from group consisting of a mouse, a hamster and a rat, renders the host mammal susceptible to infection with prions which infect and cause disease in a test animals selected from the group consisting of a human, a cow and a sheep;
   wherein the PrP gene comprises a sequence of a native PrP gene of the host mammal that has one or more, but not all, its codons that differ from a PrP gene of the test animal replaced with a corresponding codon of the PrP gene of the test animal; and
   further wherein the host animal exhibits symptoms of prion disease within 200 days or less after inoculation with a prion that infects and causes prion disease in said test animal.

8. The artificial PrP gene of claim 7 wherein the host mammal is a mouse and the test animal is a human.

9. The artificial PrP gene of claim 8 wherein from 1 to 27 of the mouse PrP codons that differ from human PrP codons is replaced with a corresponding human PrP codon.

10. The artificial PrP gene of claim 7, wherein the host animal is a mouse and the test animal is a sheep.

11. The artificial gene of claim 10 wherein the PrP gene of the mouse has from 1 to 32 of its codons which differ from the codons of a sheep PrP gene replaced with a corresponding sheep PrP codon.

12. The artificial PrP gene of claim 7, wherein the host animal is a mouse and the test animal is a cow.

13. The artificial PrP gene of claim 12 wherein the PrP gene of the mouse has from 1 to 39 of its codons which differ from the codons of a cow PrP gene replaced with corresponding cow PrP codon.

14. A method of making an artificial PrP gone characterized in that when said PrP gene is inserted into the genome of a host mammal selected from the group consisting of a mouse, a hamster, and a rat, renders the host mammal susceptible to infection with prions which infect and cause disease in a test animal selected from the group consisting of a human, a cow and a sheep, comprising
   preparing a PrP gene of the host mammal; and
   replacing one or more, but not all, of the codons of the PrP gone of the host animal that differ from a PrP gene of the test animal with a corresponding codon of the PrP gene of the test animal;
   wherein when said artificial PrP gone is expressed in the host mammal, said mammal exhibits symptoms of prion disease within 200 days or less after inoculation with a prion that infects and causes prion disease in said test animal.

15. The method of claim 14 wherein the host mammal is a mouse and the test animal is a human.

16. The method of claim 15 wherein from 1 to 27 of the mouse PrP codons that differ from human PrP codons is replaced with a corresponding human PrP codon.

17. The method of claim 14 wherein the host mammal is a mouse and the test animal is a sheep.

18. The method of claim 17 wherein the PrP gene of the mouse has from 1 to 32 of its codons which differ from the codons of a sheep PrP gene replaced with a corresponding sheep PrP codon.

19. The method of claim 14 wherein the host mammal is a mouse and the test animal is a cow.

20. The method of claim 19 wherein the PrP gene of the mouse has from 1 to 39 of its codons which differ from the codons of a cow PrP gene replaced with a corresponding cow PrP codon.

21. A method of making a transgenic mouse having a genome comprised of an artificial PrP gene which when expressed renders the transgenic mouse susceptible to infection with prions which infect and cause disease in a human, comprising:

inserting the artificial PrP gene of claim 9 into a mouse zygote capable of generating a transgenic mouse;

placing said mouse zygote in a host female mouse;

allowing said mouse zygote to grow to term;

thereby generating a transgenic mouse having the artificial PrP gene operably inserted into the genome of the mouse.

22. The method of claim 21 wherein the PrP gene is MHu2M.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 254 amino acids
( B ) TYPE: amino acid
( C ) STRANDEDNESS: single
( D ) TOPOLOGY: linear 5,565,186

(ii) MOLECULE TYPE: peptide (vi) ORIGINAL SOURCE:
  (A) ORGANISM: MOUSE PRION PROTEIN, MoPrP (xi) SEQUENCE DESCRIPTION: SEQ ID NO:1:

| Met | Ala | Asn | Leu | Gly | Tyr | Trp | Leu | Leu | Ala | Leu | Phe | Val | Thr | Met | Trp |
|---|---|---|---|---|---|---|---|---|---|---|---|---|---|---|---|
| 1 | | | | 5 | | | | | 10 | | | | | 15 | |
| Thr | Asp | Val | Gly | Leu | Cys | Lys | Lys | Arg | Pro | Lys | Pro | Gly | Gly | Trp | Asn |
| | | | 20 | | | | | 25 | | | | | 30 | | |
| Thr | Gly | Gly | Ser | Arg | Tyr | Pro | Gly | Gln | Gly | Ser | Pro | Gly | Gly | Asn | Arg |
| | | 35 | | | | | 40 | | | | | 45 | | | |
| Tyr | Pro | Pro | Gln | Gly | Gly | Thr | Trp | Gly | Gln | Pro | His | Gly | Gly | Gly | Trp |
| | 50 | | | | | 55 | | | | | 60 | | | | |
| Gly | Gln | Pro | His | Gly | Gly | Ser | Trp | Gly | Gln | Pro | His | Gly | Gly | Ser | Trp |
| 65 | | | | | 70 | | | | | 75 | | | | | 80 |
| Gly | Gln | Pro | His | Gly | Gly | Gly | Trp | Gly | Gln | Gly | Gly | Gly | Thr | His | Asn |
| | | | | 85 | | | | | 90 | | | | | 95 | |
| Gln | Trp | Asn | Lys | Pro | Ser | Lys | Pro | Lys | Thr | Asn | Leu | Lys | His | Val | Ala |
| | | | 100 | | | | | 105 | | | | | 110 | | |
| Gly | Ala | Ala | Ala | Ala | Gly | Ala | Val | Val | Gly | Gly | Leu | Gly | Gly | Tyr | Met |
| | | 115 | | | | | 120 | | | | | 125 | | | |
| Leu | Gly | Ser | Ala | Met | Ser | Arg | Pro | Met | Ile | His | Phe | Gly | Asn | Asp | Trp |
| | 130 | | | | | 135 | | | | | 140 | | | | |
| Glu | Asp | Arg | Tyr | Tyr | Arg | Glu | Asn | Met | Tyr | Arg | Tyr | Pro | Asn | Gln | Val |
| 145 | | | | | 150 | | | | | 155 | | | | | 160 |
| Tyr | Tyr | Arg | Pro | Val | Asp | Gln | Tyr | Ser | Asn | Gln | Asn | Asn | Phe | Val | His |
| | | | | 165 | | | | | 170 | | | | | 175 | |
| Asp | Cys | Val | Asn | Ile | Thr | Ile | Lys | Gln | His | Thr | Val | Thr | Thr | Thr | Thr |
| | | | 180 | | | | | 185 | | | | | 190 | | |
| Lys | Gly | Glu | Asn | Phe | Thr | Glu | Thr | Asp | Val | Lys | Met | Met | Glu | Arg | Val |
| | | 195 | | | | | 200 | | | | | 205 | | | |
| Val | Glu | Gln | Met | Cys | Val | Thr | Gln | Tyr | Gln | Lys | Glu | Ser | Gln | Ala | Tyr |
| | 210 | | | | | 215 | | | | | 220 | | | | |
| Tyr | Asp | Gly | Arg | Arg | Ser | Ser | Ser | Thr | Val | Leu | Phe | Ser | Ser | Pro | Pro |
| 225 | | | | | 230 | | | | | 235 | | | | | 240 |
| Val | Ile | Leu | Leu | Ile | Ser | Phe | Leu | Ile | Phe | Leu | Ile | Val | Gly | | |
| | | | | 245 | | | | | 250 | | | | | | |

(2) INFORMATION FOR SEQ ID NO:2:

(i) SEQUENCE CHARACTERISTICS:
    (A) LENGTH: 253 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: HUMAN PRION PROTEIN, HuPrP (xi) SEQUENCE DESCRIPTION: SEQ ID NO:2:

| Met | Ala | Asn | Leu | Gly | Cys | Trp | Met | Leu | Val | Leu | Phe | Val | Ala | Thr | Trp |
|---|---|---|---|---|---|---|---|---|---|---|---|---|---|---|---|
| 1 | | | | 5 | | | | | 10 | | | | | 15 | |
| Ser | Asp | Leu | Gly | Leu | Cys | Lys | Lys | Arg | Pro | Lys | Pro | Gly | Gly | Trp | Asn |
| | | | 20 | | | | | 25 | | | | | 30 | | |
| Thr | Gly | Gly | Ser | Arg | Tyr | Pro | Gly | Gln | Gly | Ser | Pro | Gly | Gly | Asn | Arg |
| | | 35 | | | | | 40 | | | | | 45 | | | |

|     |     |     |     |     |     |     |     |     |     |     |     |     |     |     |
| --- | --- | --- | --- | --- | --- | --- | --- | --- | --- | --- | --- | --- | --- | --- |
| Tyr | Pro 50 | Pro | Gln | Gly | Gly 55 | Gly | Trp | Gly | Gln | Pro 60 | His | Gly | Gly | Gly |
| Trp 65 | Gly | Gln | Pro | His 70 | Gly | Gly | Gly | Trp | Gly 75 | Gln | Pro | His | Gly | Gly Gly 80 |
| Trp | Gly | Gln | Pro | His 85 | Gly | Gly | Gly | Trp | Gly 90 | Gln | Gly | Gly | Gly | Thr His 95 |
| Ser | Gln | Trp | Asn 100 | Lys | Pro | Ser | Lys | Pro 105 | Lys | Thr | Asn | Met | Lys 110 | His Met |
| Ala | Gly | Ala 115 | Ala | Ala | Ala | Gly | Ala 120 | Val | Val | Gly | Gly | Leu 125 | Gly | Gly Tyr |
| Met | Leu 130 | Gly | Ser | Ala | Met | Ser 135 | Arg | Pro | Ile | Ile | His 140 | Phe | Gly | Ser Asp |
| Tyr 145 | Glu | Asp | Arg | Tyr | Tyr 150 | Arg | Glu | Asn | Met | His 155 | Arg | Tyr | Pro | Asn Gln 160 |
| Val | Tyr | Tyr | Arg | Pro 165 | Met | Asp | Glu | Tyr | Ser 170 | Asn | Gln | Asn | Asn | Phe Val 175 |
| His | Asp | Cys | Val 180 | Asn | Ile | Thr | Ile | Lys 185 | Gln | His | Thr | Val | Thr 190 | Thr Thr |
| Thr | Lys | Gly 195 | Glu | Asn | Phe | Thr | Glu 200 | Thr | Asp | Val | Lys | Met 205 | Met | Glu Arg |
| Val | Val 210 | Glu | Gln | Met | Cys | Ile 215 | Thr | Gln | Tyr | Glu | Arg 220 | Glu | Ser | Gln Ala |
| Tyr 225 | Tyr | Gln | Arg | Gly | Ser 230 | Ser | Met | Val | Leu | Phe 235 | Ser | Ser | Pro | Pro Val 240 |
| Ile | Leu | Leu | Ile | Ser 245 | Phe | Leu | Ile | Phe | Leu 250 | Ile | Val | Gly |     |     |

(2) INFORMATION FOR SEQ ID NO:3:

( i ) SEQUENCE CHARACTERISTICS:
        ( A ) LENGTH: 263 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: BOVINE PRION PROTEIN, BoPrP ( x i ) SEQUENCE DESCRIPTION: SEQ ID NO:3:

|     |     |     |     |     |     |     |     |     |     |     |     |     |     |     |
| --- | --- | --- | --- | --- | --- | --- | --- | --- | --- | --- | --- | --- | --- | --- |
| Met 1 | Val | Lys | Ser | His 5 | Ile | Gly | Ser | Trp | Ile 10 | Leu | Val | Leu | Phe | Val Ala 15 |
| Met | Trp | Ser | Asp 20 | Val | Gly | Leu | Cys | Lys 25 | Lys | Arg | Pro | Lys | Pro 30 | Gly Gly |
| Trp | Asn | Thr 35 | Gly | Gly | Ser | Arg | Tyr 40 | Pro | Gly | Gln | Gly | Ser 45 | Pro | Gly Gly |
| Asn | Arg | Tyr | Pro 50 | Pro | Gln | Gly | Gly 55 | Gly | Trp | Gly | Gln | Pro 60 | His | Gly |
| Gly Gly 65 | Trp | Gly | Gln | Pro 70 | His | Gly | Gly | Gly | Trp 75 | Gly | Gln | Pro | His 80 | Gly |
| Gly | Gly | Trp | Gly | Gln 85 | Pro | His | Gly | Gly | Gly 90 | Trp | Gly | Gln | Pro | His 95 Gly |
| Gly | Gly | Gly | Trp 100 | Gly | Gln | Gly | Gly | Thr 105 | His | Gly | Gln | Trp | Asn 110 | Lys Pro |
| Ser | Lys | Pro 115 | Lys | Thr | Asn | Met | Lys 120 | His | Val | Ala | Gly | Ala 125 | Ala | Ala Ala |
| Gly | Ala | Val | Val | Gly | Gly | Leu | Gly | Gly | Tyr | Met | Leu | Gly | Ser | Ala Met |

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |
| Ser<br>145 | Arg | Pro | Leu | Ile | His<br>150 | Phe | Gly | Ser | Asp | Tyr<br>155 | Glu | Asp | Arg | Tyr | Tyr<br>160 |
| Arg | Glu | Asn | Met | His<br>165 | Arg | Tyr | Pro | Asn | Gln<br>170 | Val | Tyr | Tyr | Arg | Pro<br>175 | Val |
| Asp | Gln | Tyr | Ser<br>180 | Asn | Gln | Asn | Asn | Phe<br>185 | Val | His | Asp | Cys<br>190 | Val | Asn | Ile |
| Thr | Val | Lys<br>195 | Glu | His | Thr | Val | Thr<br>200 | Thr | Thr | Thr | Lys | Gly<br>205 | Glu | Asn | Phe |
| Thr | Glu<br>210 | Thr | Asp | Ile | Lys | Met<br>215 | Met | Glu | Arg | Val | Val<br>220 | Glu | Gln | Met | Cys |
| Val<br>225 | Thr | Gln | Tyr | Gln | Lys<br>230 | Glu | Ser | Gln | Ala | Tyr<br>235 | Tyr | Asp | Gln | Gly | Ala<br>240 |
| Ser | Val | Ile | Leu | Phe<br>245 | Ser | Ser | Pro | Pro | Val<br>250 | Ile | Leu | Leu | Ile | Ser<br>255 | Phe |
| Leu | Ile | Phe | Leu<br>260 | Ile | Val | Gly |     |     |     |     |     |     |     |     |     |

( 2 ) INFORMATION FOR SEQ ID NO:4:

( i ) SEQUENCE CHARACTERISTICS:
       ( A ) LENGTH: 255 amino acids
       ( B ) TYPE: amino acid
       ( C ) STRANDEDNESS: single
       ( D ) TOPOLOGY: linear ( i i ) MOLECULE TYPE: peptide ( v i ) ORIGINAL SOURCE:
       ( A ) ORGANISM: SHEEP PRION PROTEIN, ShPrP ( x i ) SEQUENCE DESCRIPTION: SEQ ID NO:4:

| Met<br>1 | Val | Lys | Ser | His<br>5 | Ile | Gly | Ser | Trp | Ile<br>10 | Leu | Val | Leu | Phe | Val<br>15 | Ala |
| --- | --- | --- | --- | --- | --- | --- | --- | --- | --- | --- | --- | --- | --- | --- | --- |
| Met | Trp | Ser | Asp<br>20 | Val | Gly | Leu | Cys | Lys<br>25 | Lys | Arg | Pro | Lys | Pro<br>30 | Gly | Gly |
| Trp | Asn | Thr<br>35 | Gly | Gly | Ser | Arg | Tyr<br>40 | Pro | Gly | Gln | Gly | Ser<br>45 | Pro | Gly | Gly |
| Asn | Arg<br>50 | Tyr | Pro | Pro | Gln | Gly<br>55 | Gly | Gly | Gly | Trp | Gly<br>60 | Gln | Pro | His | Gly |
| Gly<br>65 | Gly | Trp | Gly | Gln | Pro<br>70 | His | Gly | Gly | Gly | Trp<br>75 | Gly | Gln | Pro | His | Gly<br>80 |
| Gly | Ser | Trp | Gly | Gln<br>85 | Pro | His | Gly | Gly | Gly<br>90 | Gly | Trp | Gly | Gln | Gly<br>95 | Gly |
| Ser | His | Ser | Gln<br>100 | Trp | Asn | Lys | Pro | Ser<br>105 | Lys | Pro | Lys | Thr | Asn<br>110 | Met | Lys |
| His | Val | Ala | Gly<br>115 | Ala | Ala | Ala | Ala | Gly<br>120 | Ala | Val | Val | Gly<br>125 | Gly | Leu | Gly |
| Gly | Tyr | Met<br>130 | Leu | Gly | Ser | Ala | Met<br>135 | Ser | Arg | Pro | Leu | Ile<br>140 | His | Phe | Gly |
| Asn<br>145 | Asp | Tyr | Glu | Asp | Arg<br>150 | Tyr | Tyr | Arg | Glu | Asn<br>155 | Met | Tyr | Arg | Tyr | Pro<br>160 |
| Asn | Gln | Val | Tyr | Tyr<br>165 | Arg | Pro | Val | Asp | Gln<br>170 | Tyr | Ser | Asn | Gln | Asn<br>175 | Asn |
| Phe | Val | His | Asp<br>180 | Cys | Val | Asn | Ile | Thr<br>185 | Val | Lys | Gln | His | Thr<br>190 | Val | Thr |
| Thr | Thr | Thr<br>195 | Lys | Gly | Glu | Asn | Phe<br>200 | Thr | Glu | Thr | Asp | Ile<br>205 | Lys | Ile | Met |

-continued

| Glu | Arg 210 | Val | Val | Glu | Gln | Met 215 | Cys | Ile | Thr | Gln | Tyr 220 | Gln | Arg | Glu | Ser |
| Gln 225 | Ala | Tyr | Tyr | Gln | Arg 230 | Gly | Ala | Ser | Val | Ile 235 | Leu | Phe | Ser | Ser | Pro 240 |
| Pro | Val | Ile | Leu | Leu 245 | Ile | Ser | Phe | Leu | Ile 250 | Phe | Leu | Ile | Val | Gly 255 | |